(12) United States Patent
Choi et al.

(10) Patent No.: US 11,351,224 B2
(45) Date of Patent: Jun. 7, 2022

(54) PHARMACEUTICAL COMPOSITION FOR PREVENTING AND TREATING TRANSPLANT REJECTION

(71) Applicant: IUCF-HYU (INDUSTRY-UNIVERSITY COOPERATION FOUNDATION HANYANG UNIVERSITY), Seoul (KR)

(72) Inventors: Je-Min Choi, Seoul (KR); Sangho Lim, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 119 days.

(21) Appl. No.: 16/544,671

(22) Filed: Aug. 19, 2019

(65) Prior Publication Data

US 2020/0054713 A1 Feb. 20, 2020

Related U.S. Application Data

(63) Continuation-in-part of application No. 15/753,915, filed as application No. PCT/KR2016/009201 on Aug. 19, 2016.

(30) Foreign Application Priority Data

Aug. 21, 2015 (KR) .......................... 10-2015-0117966
Aug. 19, 2016 (KR) .......................... 10-2016-0105642

(51) Int. Cl.
  *A61P 37/06* (2006.01)
  *A61K 38/10* (2006.01)
  *A61K 38/08* (2019.01)
  *A61K 38/17* (2006.01)

(52) U.S. Cl.
  CPC .......... *A61K 38/1774* (2013.01); *A61K 38/08* (2013.01); *A61K 38/10* (2013.01); *A61P 37/06* (2018.01)

(58) Field of Classification Search
  None
  See application file for complete search history.

(56) References Cited

U.S. PATENT DOCUMENTS

| 5,786,152 | A | 7/1998 | Marengere et al. | |
| 7,723,299 | B2* | 5/2010 | Lee | A61P 43/00 514/1.2 |
| 2007/0105775 | A1 | 5/2007 | Lee et al. | |
| 2010/0322893 | A1 | 12/2010 | Franks et al. | |
| 2011/0008377 | A1* | 1/2011 | Collisson | A61P 37/04 424/185.1 |
| 2019/0202888 | A1 | 7/2019 | Choi et al. | |

FOREIGN PATENT DOCUMENTS

| KR | 10-2008-0084937 | 9/2008 |
| KR | 10-2010-0105551 | 9/2010 |
| KR | 10-2014-0046994 | * 4/2014 |
| KR | 10-2015-0014443 | 2/2015 |
| WO | 95/33770 | 12/1995 |
| WO | WO 2009/058564 | 5/2009 |
| WO | WO 2013/169338 | 11/2013 |
| WO | WO 2017/0034244 | 3/2017 |

OTHER PUBLICATIONS

Li et al (Int J Mol Sci 16: 19518-19536, Aug. 18, 2015).*
Li et al (Am J Transplant 5: 978-986, 2005).*
Choi et al., "Intranasal delivery of the cytoplasmic domain of CTLA-4 using a novel protein transduction domain prevents allergic inflammation", Nature Medicine, vol. 12, No. 5, May 2006: 574-579.
GenBank: AAF02499.1, cytotoxic T-lymphocyte activated protein 4 [*Homo sapiens*], NCBI, found at https://www.ncbi.nlm.nih.gov/protein/6049193?sat=4&satkey=39333799, 1 page.
International Search Report for PCT/KR2016/009201, dated Nov. 14, 2016, 6 pages.
Li et al., "Intracellular Delivery of Molecular Cargo Using Cell-Penetrating Peptides and the Combination Strategies", Int. J. Mol. Sci., 2015, 16:19518-19536.
Lim et al., "dNP2 is a blood-brain barrier-permeable peptide enabling ctCTLA-4 protein delivery to ameliorate experimental autoimmune encephalomyelitis", Nature Communications, 6:8244, DOI: 10.1038/ncomms9244, pp. 1-13.

* cited by examiner

*Primary Examiner* — Gregory S Emch
*Assistant Examiner* — Aditi Dutt
(74) *Attorney, Agent, or Firm* — Sughrue Mion, PLLC

(57) ABSTRACT

The composition of the present invention can inhibit homologous human T cell reaction and the phenomenon of infiltration which reduces skin graft damage in vivo, thereby enabling prompt, rapid and effective graft rejection prevention or treatment effects at a low concentration. In addition, the present invention has advantages of successfully controlling in vivo human T cell reactions, as compared with conventional therapeutic agents, thus providing few side effects, the possibilities of local high-dose administration of therapeutic agents and potentially new treatments and prescriptions.

5 Claims, 23 Drawing Sheets

Specification includes a Sequence Listing.

SEQUENCE LISTING

```
<160> NUMBER OF SEQ ID NOS: 26

<210> SEQ ID NO 1
<211> LENGTH: 36
<212> TYPE: PRT
<213> ORGANISM: Artificial Sequence
<220> FEATURE:
<223> OTHER INFORMATION: ctCTLA-4

<400> SEQUENCE: 1

Lys Met Leu Lys Lys Arg Ser Pro Leu Thr Thr Gly Val Tyr Val Lys
1               5                   10                  15

Met Pro Pro Thr Glu Pro Glu Cys Glu Lys Gln Phe Gln Pro Tyr Phe
            20                  25                  30

Ile Pro Ile Asn
        35

<210> SEQ ID NO 2
<211> LENGTH: 10
<212> TYPE: PRT
<213> ORGANISM: Artificial Sequence
<220> FEATURE:
<223> OTHER INFORMATION: ctCTLA-4 fm1

<400> SEQUENCE: 2

Tyr Val Lys Met Pro Pro Thr Glu Pro Glu
1               5                   10

<210> SEQ ID NO 3
<211> LENGTH: 6
<212> TYPE: PRT
<213> ORGANISM: Artificial Sequence
<220> FEATURE:
<223> OTHER INFORMATION: ctCTLA-4 fm2

<400> SEQUENCE: 3

Tyr Phe Ile Pro Ile Asn
1               5

<210> SEQ ID NO 4
<211> LENGTH: 16
<212> TYPE: PRT
<213> ORGANISM: Artificial Sequence
```

```
<220> FEATURE:
<223> OTHER INFORMATION: ctCTLA-4 fm3

<400> SEQUENCE: 4

Tyr Val Lys Met Pro Pro Thr Glu Pro Glu Tyr Phe Ile Pro Ile Asn
1               5                   10                  15

<210> SEQ ID NO 5
<211> LENGTH: 36
<212> TYPE: PRT
<213> ORGANISM: Artificial Sequence
<220> FEATURE:
<223> OTHER INFORMATION: ctCTLA-4 1YF

<400> SEQUENCE: 5

Lys Met Leu Lys Lys Arg Ser Pro Leu Thr Thr Gly Val Phe Val Lys
1               5                   10                  15

Met Pro Pro Thr Glu Pro Glu Cys Glu Lys Gln Phe Gln Pro Tyr Phe
            20                  25                  30

Ile Pro Ile Asn
        35

<210> SEQ ID NO 6
<211> LENGTH: 36
<212> TYPE: PRT
<213> ORGANISM: Artificial Sequence
<220> FEATURE:
<223> OTHER INFORMATION: ctCTLA-4 2YF

<400> SEQUENCE: 6

Lys Met Leu Lys Lys Arg Ser Pro Leu Thr Thr Gly Val Tyr Val Lys
1               5                   10                  15

Met Pro Pro Thr Glu Pro Glu Cys Glu Lys Gln Phe Gln Pro Phe Phe
            20                  25                  30

Ile Pro Ile Asn
        35

<210> SEQ ID NO 7
<211> LENGTH: 36
<212> TYPE: PRT
<213> ORGANISM: Artificial Sequence
<220> FEATURE:
<223> OTHER INFORMATION: ctCTLA-4 DYF

<400> SEQUENCE: 7

Lys Met Leu Lys Lys Arg Ser Pro Leu Thr Thr Gly Val Phe Val Lys
1               5                   10                  15

Met Pro Pro Thr Glu Pro Glu Cys Glu Lys Gln Phe Gln Pro Phe Phe
            20                  25                  30

Ile Pro Ile Asn
        35

<210> SEQ ID NO 8
<211> LENGTH: 24
<212> TYPE: PRT
<213> ORGANISM: Artificial Sequence
<220> FEATURE:
<223> OTHER INFORMATION: dNP2

<400> SEQUENCE: 8

Lys Ile Lys Lys Val Lys Lys Lys Gly Arg Lys Gly Ser Lys Ile Lys
1               5                   10                  15

Lys Val Lys Lys Lys Gly Arg Lys
```

<210> SEQ ID NO 9
<211> LENGTH: 11
<212> TYPE: PRT
<213> ORGANISM: Artificial Sequence
<220> FEATURE:
<223> OTHER INFORMATION: Hph-1

<400> SEQUENCE: 9

Tyr Ala Arg Val Arg Arg Arg Gly Pro Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: HIV-1 tat(47-57), TAT

<400> SEQUENCE: 10

Tyr Gly Arg Lys Lys Arg Arg Gln Arg Arg Arg
1               5                   10

<210> SEQ ID NO 11
<211> LENGTH: 27
<212> TYPE: PRT
<213> ORGANISM: Artificial Sequence
<220> FEATURE:
<223> OTHER INFORMATION: Transportan

<400> SEQUENCE: 11

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 12
<211> LENGTH: 21
<212> TYPE: PRT
<213> ORGANISM: Artificial Sequence
<220> FEATURE:
<223> OTHER INFORMATION: pep-1

<400> SEQUENCE: 12

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 13
<211> LENGTH: 18
<212> TYPE: PRT
<213> ORGANISM: Artificial Sequence
<220> FEATURE:
<223> OTHER INFORMATION: pVEC

<400> SEQUENCE: 13

Leu Leu Ile Ile Leu Arg Arg Arg Ile Arg Lys Gln Ala His Ala His
1               5                   10                  15

Ser Lys

<210> SEQ ID NO 14
<211> LENGTH: 22
<212> TYPE: PRT

```
<213> ORGANISM: Artificial Sequence
<220> FEATURE:
<223> OTHER INFORMATION: M918

<400> SEQUENCE: 14

Met Val Thr Val Leu Phe Arg Arg Leu Arg Ile Arg Arg Ala Cys Gly
1               5                   10                  15

Pro Pro Arg Val Arg Val
            20

<210> SEQ ID NO 15
<211> LENGTH: 21
<212> TYPE: PRT
<213> ORGANISM: Artificial Sequence
<220> FEATURE:
<223> OTHER INFORMATION: TP10

<400> SEQUENCE: 15

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 16
<211> LENGTH: 34
<212> TYPE: PRT
<213> ORGANISM: Artificial Sequence
<220> FEATURE:
<223> OTHER INFORMATION: VP22

<400> SEQUENCE: 16

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu

<210> SEQ ID NO 17
<211> LENGTH: 20
<212> TYPE: PRT
<213> ORGANISM: Artificial Sequence
<220> FEATURE:
<223> OTHER INFORMATION: Buforin2

<400> SEQUENCE: 17

Thr Arg Ser Ser Arg Ala Gly Leu Gln Phe Pro Val Gly Arg Val His
1               5                   10                  15

Arg Leu Leu Arg
            20

<210> SEQ ID NO 18
<211> LENGTH: 30
<212> TYPE: PRT
<213> ORGANISM: Artificial Sequence
<220> FEATURE:
<223> OTHER INFORMATION: KALA

<400> SEQUENCE: 18

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30
```

```
<210> SEQ ID NO 19
<211> LENGTH: 35
<212> TYPE: PRT
<213> ORGANISM: Artificial Sequence
<220> FEATURE:
<223> OTHER INFORMATION: CL22

<400> SEQUENCE: 19

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Asn Ile Leu
            20                  25                  30

Lys Gly Lys
        35

<210> SEQ ID NO 20
<211> LENGTH: 42
<212> TYPE: PRT
<213> ORGANISM: Artificial Sequence
<220> FEATURE:
<223> OTHER INFORMATION: Crotamine

<400> SEQUENCE: 20

Tyr Lys Gln Cys His Lys Lys Gly Gly His Cys Phe Pro Lys Glu Lys
1               5                   10                  15

Ile Cys Leu Pro Pro Ser Ser Asp Phe Gly Lys Met Asp Cys Arg Trp
            20                  25                  30

Arg Trp Lys Cys Cys Lys Lys Gly Ser Gly
        35                  40

<210> SEQ ID NO 21
<211> LENGTH: 67
<212> TYPE: DNA
<213> ORGANISM: Artificial Sequence
<220> FEATURE:
<223> OTHER INFORMATION: dNP2-ctCTLA4 forward primer

<400> SEQUENCE: 21
aagattaaga aagtcaagaa gaaaggaaga aaggaattct acccatacga tgttccagat    60
tacgcta                                                              67

<210> SEQ ID NO 22
<211> LENGTH: 67
<212> TYPE: DNA
<213> ORGANISM: Artificial Sequence
<220> FEATURE:
<223> OTHER INFORMATION: dNP2-ctCTLA-4 forward primer

<400> SEQUENCE: 22
gctagcaaga ttaagaaagt caagaagaaa ggaagaaagg atccaagat taagaaagtc    60 aagaaga                                                              67

<210> SEQ ID NO 23
<211> LENGTH: 73
<212> TYPE: DNA
<213> ORGANISM: Artificial Sequence
<220> FEATURE:
<223> OTHER INFORMATION: TAT-ctCTLA-4 forward primer

<400> SEQUENCE: 23
gctagctatg gacgcaagaa gcgccgccag cgccgccgcg gatcctaccc atacgatgtt    60
ccagattacg cta                                                       73
```

```
<210> SEQ ID NO 24
<211> LENGTH: 67
<212> TYPE: DNA
<213> ORGANISM: Artificial Sequence
<220> FEATURE:
<223> OTHER INFORMATION: Hph-1-ctCTLA-4 primer

<400> SEQUENCE: 24
tatgcgcgtg tgcgacgtcg tggcccacgt cgaggatcct acccatacga tgttccagat    60
tacgcta                                                              67

<210> SEQ ID NO 25
<211> LENGTH: 61
<212> TYPE: DNA
<213> ORGANISM: Artificial Sequence
<220> FEATURE:
<223> OTHER INFORMATION: dNP2-EGFP primer

<400> SEQUENCE: 25
aagattaaga aagtcaagaa gaaaggaaga aaggtgagca agggcgagga gctgttcacc    60
g                                                                    61

<210> SEQ ID NO 26
<211> LENGTH: 67
<212> TYPE: DNA
<213> ORGANISM: Artificial Sequence
<220> FEATURE:
<223> OTHER INFORMATION: dNP2-EGFP primer

<400> SEQUENCE: 26
gctagcaaga ttaagaaagt caagaagaaa ggaagaaagg gatccaagat taagaaagtc    60
aagaaga                                                              67
```

PHARMACEUTICAL COMPOSITION FOR PREVENTING AND TREATING TRANSPLANT REJECTION

CROSS-REFERENCE TO RELATED APPLICATIONS

This application claims priority to and is a Continuation-In-Part of U.S. application Ser. No. 15/753,915, filed on Feb. 20, 2018, entitled "PEPTIDES HAVING EFFECTS OF PREVENTING OR TREATING CENTRAL NERVOUS SYSTEM DISEASES AND PHARMACEUTICAL COMPOSITIONS FOR PREVENTING OR TREATING CENTRAL NERVOUS SYSTEM DISEASES CONTAINING SAME AS ACTIVE INGREDIENT" (now U.S. Pat. No. 11,053,295), which application claims priority and is a 371 National phase of PCT/KR2016/009201 (WO2017/034244), filed on Aug. 19, 2016 entitled "PEPTIDES HAVING EFFECTS OF PREVENTING OR TREATING CENTRAL NERVOUS SYSTEM DISEASES AND PHARMACEUTICAL COMPOSITIONS FOR PREVENTING OR TREATING CENTRAL NERVOUS SYSTEM DISEASES CONTAINING SAME AS ACTIVE INGREDIENT", which application claims priority to and the benefit of Korean Patent Application Nos. 10-2015-0117966 filed on Aug. 21, 2015 and 10-2016-0105642 filed on Aug. 19, 2016, the disclosures of which are incorporated herein by reference in their entirety. Any disclaimer that may have occurred during the prosecution of the above-referenced applications is hereby expressly rescinded, and reconsideration of all relevant art is respectfully requested.

Incorporated by reference herein in its entirety is the Sequence Listing entitled "PCT457-US-CIP01_ST25," created Aug. 7, 2019, size of 9 kilobyte.

TECHNICAL FIELD

The present invention relates to peptides having effects of preventing and treating transplant rejection and pharmaceutical compositions for preventing or treating transplant rejection containing the peptides as an active ingredient.

BACKGROUND ART

Acute xenograft immune rejection is a response in which the host non-self recognizes the grafted tissue and removes it and is involved in major histocompatibility complex (MHC) or minor histocompatibility complex. Rejection relates to both cell-mediated immunity and humoral immunity, but relative contributions thereof depend on the type of graft response. T cell mediated reactions initiate when lymphocytes of a recipient meet MHCs of the donor, that is, immune reactions begin, when the host T cells meet the bifurcated cells in transplanted organs or bifurcated cells of the donor enter the lymph node of the recipient. Activated CD4 T cells secrete cytokines from delayed hypersensitivity to increase vascular permeability, and cause local infiltration of mononuclear cells such as lymphocytes and macrophages, and infiltrated macrophages lead to microvascular injury, tissue ischemia and destruction of graft tissues.

In addition, antibody-mediated responses to alloantigens can also result in immunological graft rejection. Hyperacute rejection occurs in the case of presence of already formed anti-donor antibodies, or kidney transplants, pregnancy (nonself MHCs originating from the fetus), or blood (platelets, white blood cells) transfusion from donors having inconsistent MHCs. In the case of rejection occurring when antibodies are formed later, although not exposed to graft antigens, B cells secrete antibodies to donor antigens with the aid of T cells, and the first targets of antibodies are the blood vessels of the graft tissues.

In general transplantation, a recipient rejects the transplanted organ, whereas, upon transplant of bone marrow or immune cells, the transplanted immune cells reject the recipient's immune system and this phenomenon is called "graft-versus-host rejection".

Several methods have been proposed to treat such rejection reactions. There are methods of removing T cells from transplanted bone marrow cells, methods of administering antibodies against CD80, CD86 and the like to inhibit reaction between T cells and antigen-presenting cells, and methods of administering antibodies against cytokines such as IL-2 and IFN-gamma. Furthermore, methods of administering compound immunosuppressants such as cyclosporin A, rapamycin and FK-506 steroid preparations have also been used. Of these methods, a method of administering compound immunosuppressants inhibiting the activation of T cells is the most widely used.

Although many compound immunosuppressants have been developed to date, cyclosporin A has the best clinical effects and is widely used for prevention of organ transplant rejection including acute transplant rejection. However, cyclosporin A is capable of treating diseases by completely inhibiting the activation of T cells when used at a high dose, but has problems of significant side effects including kidney toxicity.

Therefore, there is an urgent need to develop new methods for treating transplant rejection that do not cause side effects such as infection or toxicity while avoiding depletion of T cells.

DISCLOSURE

Technical Problem

Therefore, the present invention has been made in view of the above problems and, as a result of intensive efforts to develop methods for inhibiting transplant rejection that may occur during organ, tissue or cell transplantation for the treatment of various diseases and increasing transplantation success rates, the present invention was conceived by completing a composition, based on the peptide consisting of the amino acid sequence represented by SEQ ID NO. 1 and by identifying that, when using this, the T cell response that induces rejection during transplantation is effectively controlled, and the delivery efficiency to primary human T cells without stimulation of the cell membrane, or chemical or physical destruction is superior.

Thus, it is one object of the present invention to provide a pharmaceutical composition for preventing or treating transplant rejection.

It is another object of the present invention to provide a method for inhibiting transplant rejection using the pharmaceutical composition for preventing or treating transplant rejection.

It is another object of the present invention to provide use for the preparation of a drug for preventing or treating transplant rejection.

Technical Solution

In accordance with the present invention, the above and other objects can be accomplished by the provision of a pharmaceutical composition for preventing or treating transplant rejection containing, as an active ingredient, a peptide having an amino acid sequence represented by Sequence ID No. 1, a fragment thereof or a fusion peptide of two or more of the fragment.

The fragment may be represented by Sequence ID No. 2 or 3.

The fusion peptide may have an amino acid sequence represented by Sequence ID No. 4.

The composition may be used to inhibit transplant rejection of skin, blood, cornea, liver, lung, intestines, pancreas, heart, kidney, bone marrow, stem cells or progenitor cells.

The composition may be used to treat and prevent graft-versus-host rejection.

The composition may be used for at least one of (a) pre-transplant administration and (b) post-transplant administration.

In accordance with another aspect of the present invention, provided is a pharmaceutical composition for preventing or treating transplant rejection containing, as an active ingredient, a fusion product including a peptide having an amino acid sequence represented by Sequence ID No. 1, a fragment thereof, or a fusion peptide of two or more of the fragment, and a cell-penetrating peptide.

The fragment may have an amino acid sequence represented by Sequence ID No. 2 or Sequence ID No. 3.

The fusion peptide may have an amino acid sequence represented by Sequence ID No. 4.

The cell-penetrating peptide may include any one selected from peptides amino acid sequences represented by Sequence ID Nos. 8 to 20, DNA-bound peptides including 7 or more arginines, and polyarginine polypeptides including 6 to 8 arginines.

The cell-penetrating peptide may be a dNP2 protein of the amino acid sequence represented by Sequence ID No. 8.

The composition may be used to inhibit transplant rejection of skin, blood, cornea, liver, lung, intestines, pancreas, heart, kidney, bone marrow, stem cells or progenitor cells.

The composition may be used to treat and prevent graft-versus-host rejection.

The composition may be used for at least one of (a) pre-transplant administration and (b) post-transplant administration.

In accordance with another aspect of the present invention, provided is a method for inhibiting transplant rejection including administering a composition containing, as an active ingredient, a peptide having an amino acid sequence represented by Sequence ID No. 1, a fragment thereof or a fusion peptide of two or more of the fragment, (a) before transplant or (b) after transplant.

In accordance with another aspect of the present invention, provided is a method for inhibiting transplant rejection including administering a composition containing, as an active ingredient, a fusion product including a peptide having an amino acid sequence represented by Sequence ID No. 1, a fragment thereof or a fusion peptide of two or more of the fragment, and a cell-penetrating peptide (a) before transplant or (b) after transplant.

In accordance with another aspect of the present invention, provided is a use of a peptide having an amino acid sequence represented by Sequence ID No. 1, a fragment thereof, or a fusion peptide of two or more of the fragment, for the preparation of a drug for preventing or treating transplant rejection.

In accordance with another aspect of the present invention, provided is a use of a fusion product including a peptide having an amino acid sequence represented by Sequence ID No. 1, a fragment thereof, or a fusion peptide of two or more of the fragment, and a cell-penetrating peptide, for the preparation of a drug for preventing or treating transplant rejection.

Advantageous Effects

The composition of the present invention can inhibit homologous human T cell reaction and the phenomenon of infiltration which reduces skin graft damage in vivo, and thus has prompt, rapid and effective graft rejection prevention or treatment effects only with a low content.

In addition, the present invention has advantages of successfully controlling in vivo human T cell reactions, as compared with conventional therapeutic agents, thus having advantages of few side effects, and the possibilities of local high-dose administration of therapeutic agents to provide potential new treatment and prescription.

BRIEF DESCRIPTION OF THE DRAWINGS

The above and other objects, features and other advantages of the present invention will be more clearly understood from the following detailed description taken in conjunction with the accompanying drawings, in which:

FIGS. 3B and 3D are shown using bi-directional ANOVA for statistical analysis, ***means $p<0.001$, and n.s is an insignificant number;

FIGS. 12A and 12B are graphs showing results of flow cytometry after staining with anti-CD4, anti-CD8, anti-CD69 and anti-CD25 fluorescent-labeled antibodies, and FIG. 12C is a graph showing results of analysis of IL-2 concentrations of the culture supernatant using an IL-2 ELISA kit;

BEST MODE

Figure 1A:
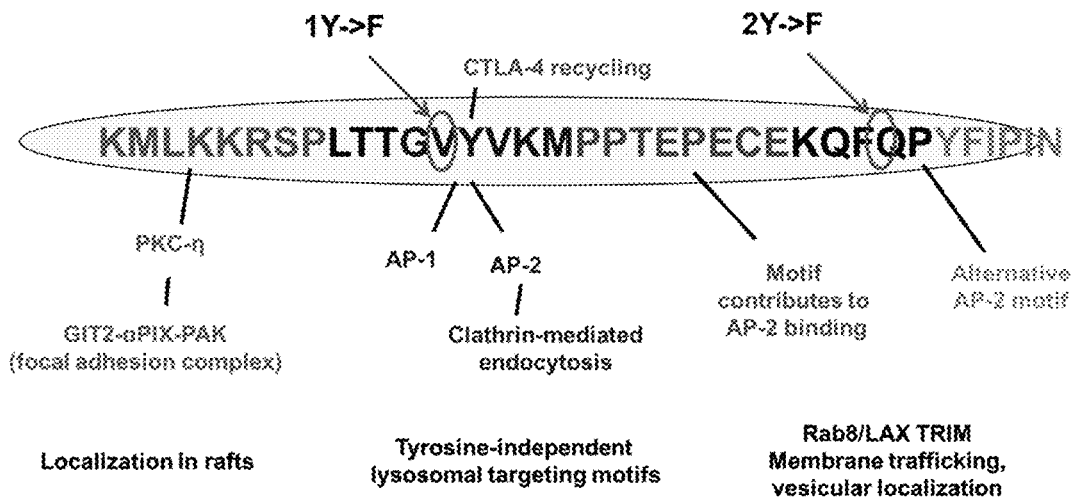
FIG. 1A shows identification results regarding a fragment of the cytoplasmic domain in the CTLA-4 protein according to the present invention and variation parts.
Figure 1B:
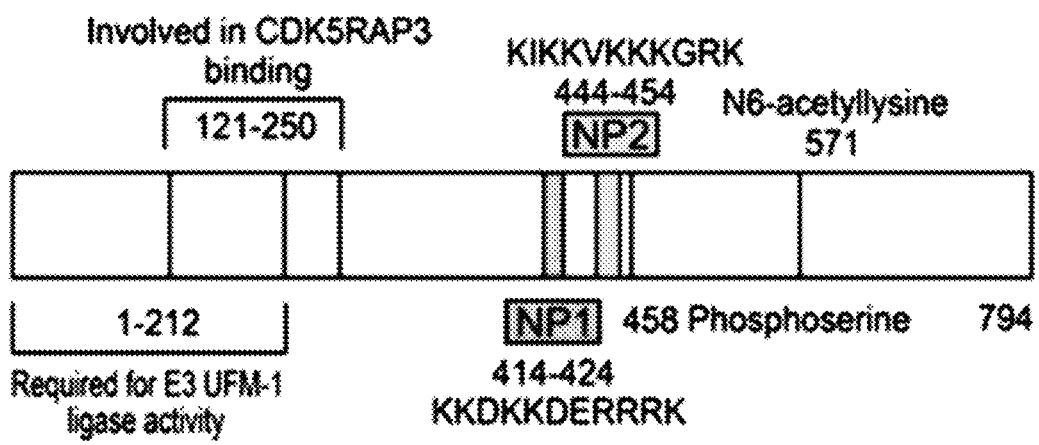
FIG. 1B shows identification results regarding dNP2, a human-derived cell-penetrating peptide according to the present invention.

Hereinafter, several aspects and various embodiments of the present invention will be described in more detail.

Immunity refers to the action of recognizing and removing external antigenic substances present in the body to protect the body from external antigens. The immune response can be divided into cellular immune response and humoral immune response. In the humoral immune response, antibodies secreted from B cells recognize external antigens and neutralize the external antigens or bind the antigens to the surface of other non-self-recognized cells, thereby facilitating phagocytosis by macrophages, or activating the complement system to increase specific immune responses. In the cell-mediated immune response, cytotoxic T cells (Tc cells) directly neutralize external antigens or secrete cytokines such as IL-2 and IFN-gamma to activate macrophages. Thus, the ability to distinguish self-antigens from non-self-antigens in the immune response is absolutely important for the body's defense system.

However, in the specific situation of transplantation of allogeneic or heterogeneous cells, tissues, organs and the like, it is necessary to suppress graft rejection (immune response) in order to prevent beneficial ex vivo rejection of the graft. For example, transplantation of allogeneic bone marrow or transplantation of hematopoietic stem cells is used as an effective method for the treatment of leukemia, myeloma, lymphoma and hematologic malignancy such as aplastic anemia. When the grafts are recognized as non-self-antigens to induce immune rejection, the graft from the donor causes damage to the recipient's tissues, skin, organs and, in serious cases, can even lead to death. A disease that causes graft rejection and damages host tissues is referred to as "graft-versus-host disease (GVHD)". For example, in the case of stem cell transplantation, a new cell (graft) transplanted in the bone marrow recognizes the patient's tissue (host) as heterogeneous, thus causing the bone marrow cells of the allogeneic donor to damage the recipient's tissues, skin, digestive organs and organs such as liver. When considering the pathogenesis of graft-versus-host disease, the antigen-presenting cells of the patient activate T cells in transplanted bone marrow cells to differentiate the same into Th1 cells and increase the secretion of cytokines such as IL-2 and IFN-gamma cytotoxic T cells. As a result, cytotoxic T cells, natural killer cells and the like are activated, and these activated cells attack the organs of the patient and cause graft-versus-host diseases. The major cause of graft-versus-host disease has been reported to be transplantation of allogeneic bone marrow or hematopoietic stem cells, in particular, the graft-versus-host disease is caused by transplantation of hematopoietic stem cells, resulting in 15 to 30% of deaths. Therefore, in order to prevent occurrence of graft-versus-host disease and to enable the graft to live for a long time, it is urgent to develop a new compound which can avoid the immune system of the recipient recognizing the foreign antigen or inhibit graft rejection (immune response).

Accordingly, the present invention has been made in an attempt to develop novel proteins that are useful for the treatment and prevention of graft rejection and/or graft-versus-host disease by inhibiting the immune response to transplanted organs, tissues or cells.

One aspect of the present invention is directed to a pharmaceutical composition for preventing or treating transplant rejection, as an active ingredient, containing a peptide having an amino acid sequence represented by Sequence ID No. 1, a fragment thereof or a fusion peptide of two or more of the fragments.

One feature of the present invention is to develop novel proteins that have excellent ability to penetrate cells, can minimize transplant rejection that may occur during transplantation of organs, tissues or cells by significantly controlling activation of human T cells, and generation, proliferation and invasion of cytokine, and can increase transplant success rates.

As used herein, the term "peptide having an amino acid sequence represented by Sequence ID No. 1" refers to a sequence derived from the cytoplasmic domain in a CTLA-4 protein, which is obtained by sequencing only a part of exon 4 of whole CTLA-4 protein derived from humans or mice. That is, the term means an amino acid sequence of a part that has an identity of 100% among amino acid sequences of CTLA-4 proteins in humans and mice. Such an amino acid sequence has a low risk of causing side effects such as immune reaction when applied to humans.

The peptide having an amino acid sequence represented by Sequence ID No. 1 is a fragment of CTLA-4 that has an activity of preventing or treating transplant rejection in the CTLA-4 protein, and also has the effect of passing through the cell membrane at a high efficiency. By using an amino acid sequence that has an identity of 100% in humans and animals (mice) except humans, the fragment can be applied to both thereof.

Specifically, the peptide having an amino acid sequence represented by Sequence ID No. 1 refers to a peptide including the $188^{th}$ amino acid residue to the $213^{th}$ amino acid sequence of the cytotoxic T lymphocyte antigen-4 (CTLA-4) protein (Sequence ID No. 1), which is hereinafter referred to as "ctCTLA-4". The peptide is a polypeptide, the N-end and C-end of which are partially deleted, in order to provide high penetration ability to the cell membrane as well as effects of preventing or treating transplant rejection.

In addition, the "fragment" of the "peptide represented by Sequence ID No. 1" may be an amino acid sequence represented by Sequence ID No. 2 or 3, which is a fragment of the cytoplasm region of the CTLA-4 protein.

The fragment of the ctCTLA-4 protein includes the $201^{st}$ amino acid residue to the $210^{th}$ amino acid sequence (Sequence ID No. 2), or the $218^{th}$ amino acid residue to the $223^{th}$ amino acid sequence of the ctCTLA-4 protein (Sequence ID No. 3), and may be a fragment of the polypeptide, the N- and C-end of which are partially deleted, in order to provide high penetration ability to the cell membrane as well as effects of preventing or treating transplant rejection.

The "fusion peptide of fragments" of "the peptide represented by Sequence ID No. 1" may be an amino acid sequence represented by Sequence ID No. 4 wherein Sequence ID No. 2 is combined with Sequence ID No. 3.

The peptide represented by Sequence ID No. 1, a fragment thereof or a fusion peptide of two or more of the fragment are very small peptides and thus have an advantage of minimizing possible biological interference.

The peptide represented by Sequence ID No. 1, a fragment thereof or a fusion peptide of two or more of the fragment may be naturally extracted, or synthesized, or produced by genetic recombination, based on DNA sequence.

The following various test results showed that the ctCTLA-4 peptide is capable of highly efficiently passing through the cell membrane and has effects of inhibiting activation of T cells and expression of chemokine receptors, of potently suppressing proliferation of human CD4 and CD8 T cells, and production of cytokines, and of inhibiting proliferation and production of effector molecules by T cells so as to minimize immunological rejection that may occur during transplantation of organs, cells or tissues.

In particular, in vivo experiments using animal models showed that ctCTLA-4 peptides have the effects of preventing or inhibiting transplant rejection of skin or vascular endothelial cells (HUVECs).

As can be seen from these experimental results, the composition of the present invention has effects of increasing regulatory T cells, inhibiting the activation of transplanted T cells through the immunosuppressive action of the increased regulatory T cells, controlling the inflammatory reaction and suppressing the immune response. Therefore, the composition of the present invention is useful as a pharmaceutical composition for inhibiting transplant rejection, and further can be widely applied to the treatment of graft rejection, graft versus host disease and the like which require suppression of the immune response.

In other words, it was identified that the peptide of Sequence ID No. 1 and the peptide of Sequence ID No. 2, 3 or 4 derived from the CTLA-4 protein can control the function of T cells without the presence of ligands capable of interacting with T cells, which indicates that successful transplantation can be promoted by controlling T cells involved in transplant rejection in transplant animal models. Accordingly, the peptide of Sequence ID No. 1 and the peptide of Sequence ID No. 2, 3 or 4 can be useful for the prevention or treatment of transplant rejection.

The term "inhibition of transplant rejection" as used herein refers to inhibition of an immune response unbeneficial to the living body caused by external antigens or self-antigens.

The peptide having the amino acid sequence shown in SEQ ID NO. 1 of the present invention, a fragment thereof and a fusion peptide of two or more of the fragment can be used to inhibit transplant rejection (immune rejection) that can occur during transplantation of cells, tissues and organs, for example, to inhibit transplant rejection of skin, blood, cornea, liver, lung, intestines, pancreas, heart, kidney, bone marrow, stem cells or progenitor cells, preferably to inhibit immune rejection that may occur during skin transplantation, bone marrow transplantation, transfusion and organ transplantation.

Accordingly, the pharmaceutical composition of the present invention can be useful for the treatment and prevention of graft rejection and/or graft-versus-host disease by inhibiting the immune response to the transplanted organs, tissues or cells.

The term "treatment" as used herein refers to stopping or delaying the progression of a disease when used in a subject with the onset of a disease and related symptoms, and the term "prevention" as used herein refers to and means stopping or delaying signs of a disease when used in a subject that does not develop disease symptoms, but has a high risk of developing the disease symptoms.

It was identified that the composition of the present invention can regulate activation of human T cells and effector functions in human skin or vascular endothelial cell (HUVEC)-grafted animal models, and inhibit secretion of IFN-γ and IL-17 in infiltration of blood and T cells to control important functions of T cells.

The composition may be used for at least one of (a) pre-transplant administration and (b) post-transplant administration. In this case, transplantation has a general meaning to describe the process of transplanting organs, tissues, cell lumps or individual cells into a recipient (host). The term "transplantation" as used herein is defined as the process of delivering viable tissue or cells from a donor to a recipient for the purpose of maintaining the functional integrity of the tissue or cell transplanted into the recipient.

The (a) pre-transplant administration includes administering the composition disclosed herein to the donor or recipient in a preparation step prior to transplantation, preferably several minutes, hours or days, or tens of days prior to surgery. For example, the (a) pre-transplant administration may be pre-treatment of organs, tissues or cells prior to transplant, and specifically includes preparing organs, tissues or cells for transplant into a host and treating the organs, tissues or cells before transplant into the host with a peptide consisting of the amino acid sequence represented by SEQ ID NO. 1, a fragment thereof, or a fusion peptide of the fragments.

The method for treating the same is to culture organs, tissues or cells for transplant in a laboratory and culture a peptide having the amino acid sequence represented by SEQ ID NO. 1, a fragment thereof or a fusion peptide of the fragments in a culture medium.

In addition, the (b) administration to the host into which the cells have been transplanted means administration during the entire procedure of graft transplant or after completion of graft transplant, and includes: during the grafting operation; during graft of extracted organs, tissues or cells into a recipient just after extraction of organs, tissues or cells from a donor; immediately after completion of graft; and several minutes, several hours, several days, tens of days, and several hundred days after the operation. For example, organs, tissues or cells for graft may be administered systemically to the grafted recipient, and may be performed at any time with or immediately after graft of grafted organs, tissues or cells. At this time, the composition of the present invention can be systemically effective, even when being administered through other sites without being directly administered to the sites where the organs, tissues or cells for graft are grafted.

The composition according to the present invention may further include an appropriate carrier, excipient and diluent which are generally used in the preparation of pharmaceutical compositions. The pharmaceutical composition according to the present invention can be formulated into oral formulations, such as powders, granules, tablets, capsules, suspensions, emulsions, syrups and aerosols, external preparations, suppositories and sterile injection solutions according to an ordinary method.

Suitable preparations known in the art are preferably those disclosed in Remington's Pharmaceutical Science (Mack Publishing Company, Easton Pa.).

Examples of the carrier, excipient and diluent, which may be incorporated in the pharmaceutical composition according to the present invention, may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate and mineral oil. The preparations can be produced using generally used diluents or excipients such as fillers, extenders, binders, wetting agents, disintegrants and surfactants. Solid preparations for oral administration include tablets, pills, powders, granules, capsules and the like. These solid preparations are produced by mixing the extract with at least one excipient, for example, starch, calcium carbonate, sucrose, lactose, gelatin or the like. In addition, apart from the simple excipient, lubricants such as magnesium stearate and talc may be used. Liquid preparations for oral administration include suspensions, liquids for internal use, emulsions, syrups and the like. Generally used diluents such as water and liquid paraffin as well as various excipients, for example, wetting agents, sweeteners, fragrances, preservatives and the like may be included. Preparations for parenteral administration include sterile aqueous solutions, non-aqueous solvents, suspensions, emulsions, lyophilized preparations and suppositories. Useful non-aqueous solvents and suspensions include propylene glycol, polyethylene glycol, vegetable oil such as olive oil, injectable ester such as ethyl oleate and the like. The base for suppositories includes Witepsol, Macrogol, Tween 61, cacao butter, laurin, glycerogelatin or the like.

The term "administration" as used herein means providing the predetermined composition according to the present invention to a subject by any suitable method.

The preferred dose of the pharmaceutical composition according to the present invention can be suitably selected by those skilled in the art according to patient's conditions and body weight, severity of disease, dosage form, and administration route and period. In order to achieve desired effects, the composition of the present invention can be administrated daily at a dose of 0.001 to 1,000 mg/kg. The composition can be administered in a single dose per day or in multiple doses per day. The dose should not be construed as limiting the scope of the present invention in any context. The pharmaceutical composition according to the present invention can be administered via various routes. All administration methods can be used, for example, oral or rectal, or by intravenous, intramuscular, subcutaneous, intrauterine, intradural or intracerebroventricular injection.

In accordance with another aspect of the present invention, provided is a pharmaceutical composition for preventing or treating transplant rejection containing, as an active ingredient, a fusion product including a peptide having an amino acid sequence represented by Sequence ID No. 1, a fragment thereof, or a fusion peptide of two or more of the fragment, and a cell-penetrating peptide.

The peptide having an amino acid sequence represented by Sequence ID No. 1, a fragment thereof or a fusion peptide of two or more of the fragment has been described above and detailed explanation thereof is thus omitted.

In an embodiment of the present invention, the cell-penetrating peptide is further incorporated into one or two sides of the peptide having an amino acid sequence represented by Sequence ID No. 1, a fragment thereof or a fusion peptide of two or more of the fragment, thereby further improving incorporation into T cells. Such a fusion product may be also referred to as "fusion protein".

The fusion product down-regulates production of cytokines in activated T-cells, and shows preventive and therapeutic effects of transplant rejection in both skin transplant animal models and vascular endothelial cell transplant animal models.

The term "fusion product" or "fusion protein", as used herein, includes ctCTLA-4 peptides, fragments thereof or fusion peptides thereof, and cell-penetrating peptides, and means covalently bonded composites formed by genetic fusion or chemical bonding thereof.

In addition, the term "genetic fusion", as used herein, means binding created by linear or covalent bonding through generic expression of DNA sequences encoding proteins.

In an embodiment of the present invention, the cell-penetrating peptide is not particularly limited and is preferably any one selected from amino acid sequences represented by Sequence ID Nos. 8 to 20, DNA-bound peptides including 7 or more arginines, and polyarginine polypeptides including 6 to 8 arginines.

Most cell-penetrating peptides are known to have excellent in vitro penetration efficiency in a variety of cell lines and are predicted to have improved cell penetration ability when bound to cargo proteins. However, in general, the cell-penetrating peptides were found to have much poorer penetration efficiency to primary cells. For this reason, cell-penetrating peptides have been greatly restricted in clinical application in humans (Simon, M. J., Gao, S., Kang, W. H., Banta, S. & Morrison, B., 3rd. TAT-mediated intracellular protein delivery to primary brain cells is dependent on glycosaminoglycan expression. Biotechnology and bioengineering 104, 10-19, doi:10.1002/bit.22377 (2009)). On the other hand, the present invention demonstrates that the effects of clinical application to humans, which could not be conventionally expected, can be significantly improved by combining the ctCTLA-4 proteins or fragments thereof with cell-penetrating peptides. In particular, when the cell-penetrating peptide is a dNP2 protein having an amino acid sequence represented by Sequence ID No. 8, activity against transplant rejection is found to be significantly improved.

Another aspect of the present invention is directed to a recombinant expression vector that includes genes encoding a fusion product including a peptide having an amino acid sequence represented by Sequence ID No. 1, a fragment thereof, or a fusion peptide of two or more of the fragment, and a cell-penetrating peptide. Alternatively, another aspect of the present invention is directed to a recombinant expression vector that includes genes encoding a fusion product including a peptide having an amino acid sequence represented by Sequence ID No. 1, a fragment thereof, or a fusion peptide of two or more of the fragment, and genes encoding the cell-penetrating peptide. The recombinant expression vector may include the cell-penetrating peptide and the peptide having an amino acid sequence represented by Sequence ID No. 1, a fragment thereof, or a fusion peptide of the fragments (Sequence ID No. 1, 2, 3 or 4), and a tag sequence to facilitate purification of the fusion product, for example, a continuous histidine codon, a maltose-binding protein codon, an Myc codon or the like, and may further include a fusion partner or the like to improve solubility of the fusion product. In addition, the recombinant expression vector may include a spacer amino acid or base sequence to stabilize the whole structure and functions of the recombinant protein, or to impart flexibility to proteins that respective genes encode. Examples of the spacer include AAY (P. M. Daftarian et al., J Trans Med 2007, 5:26), AAA, NKRK (R. P. M. Sutmuller et al., J Immunol. 2000, 165: 7308-7315), or a plurality of lysine residues in one thereof (S. Ota et al., Can Res. 62, 1471-1476, K. S. Kawamura et al., J Immunol. 2002, 168: 5709-5715), but the present invention is not limited thereto. In addition, the recombinant expression vector may include a sequence that is specifically cleaved by an enzyme, in order to remove an unnecessary part of the recombinant protein, an expression regulatory sequence, and a marker or reporter gene sequence to identify transfer into cells, but the present invention is not limited thereto.

The expression regulatory sequence used for the recombinant expression vector may be composed of regulatory domains that include promoters specific to cells, tissues or organs which target DNAs and/or RNAs are selectively transferred to or expressed in.

Another aspect of the present invention is directed to a food composition for preventing or treating transplant rejection, as an active ingredient, containing a fusion product including: a peptide having an amino acid sequence represented by Sequence ID No. 1, a fragment thereof or a fusion peptide of two or more of the fragment; and a cell-penetrating peptide.

When the composition according to the present invention is used as a food additive, it may be added alone or may be used in combination with other foods or food ingredients and may be suitably used according to conventional methods. The amount of active ingredient added can be suitably determined depending on purpose of use (prophylactic, health or therapeutic treatment). When the composition according to the present invention is used for the preparation of a food or beverage, it is generally added in an amount of 15 wt % or less, preferably 10 wt % or less, based on the total weight of the food or beverage. However, when prolonged intake is intended for the purpose of health, hygiene or health control, the amount of the active ingredient may be smaller than the lower limit of the range defined above. In addition, the active ingredient may be used in an amount higher than the upper limit of the above range because it does not cause a problem in terms of safety.

In addition to the ingredients described above, the composition according to the present invention may include a variety of nutrients, vitamins, electrolytes, flavors, colorants, pectic acid and salts thereof, alginic acid and salts thereof, organic acids, protective colloidal thickening agents, pH adjusting agents, stabilizers, antiseptics, glycerine, alcohol and carbonating agents for carbonated drinks. Further, the composition according to the present invention may include flesh for producing natural fruit juices, fruit juice drinks and vegetable drinks. This ingredient may be used alone or in combination. The proportion of this additive is not significantly important, but is generally determined within the range of 0.01 to 0.1 parts by weight with respect to 100 parts by weight of the composition according to the present invention.

Another aspect of the present invention is directed to a method for inhibiting transplant rejection including administering a composition containing, as an active ingredient, a peptide having an amino acid sequence represented by Sequence ID No. 1, a fragment thereof or a fusion peptide of two or more of the fragment (a) before transplant or (b) after transplant.

Another aspect of the present invention is directed to a method for inhibiting transplant rejection including administering a composition containing, as an active ingredient, a fusion product including a peptide having an amino acid sequence represented by Sequence ID No. 1, a fragment thereof, or a fusion peptide of two or more of the fragment, and a cell-penetrating peptide (a) before transplant or (b) after transplant.

The pharmaceutical composition can be injected in vivo or in vitro via a route such as intravenous, intraperitoneal, intramuscular, subcutaneous, intradermal, nasal, mucosal, inhalation or oral route. The application of the transfer mode can be sufficiently expanded to transfer to culture cells as well as general in vivo transfer, that is, transfer to animal cells, animal tissues and animals. There is no limitation as to plasmid size because the pharmaceutical composition is non-immunogenic and non-infectious and DNAs are not packaged in vector organisms such as retroviral or adenovirus vector organisms. Accordingly, the pharmaceutical composition can also be used for any recombinant gene expression structure with a practical size.

In this method, the amount of active ingredient administered to the donor is sufficient to enhance the viability or function of organs, tissues or cells after grafting to the recipient. In this case, the administration to the donor can be continuously performed at the time of the operation, immediately before the operation, at the pre-operation preparation step and/or the post-operative management step. The donor may be a surviving donor, a brain-dead donor, or a pre-brain-dead or post-brain-dead donor.

The present invention relates to a method including: obtaining organs, tissues or cells from a donor; retaining the obtained organs, tissues or cells in the composition; and grafting the retained organs, tissues or cells to a recipient. In the method, the amount of the active ingredient in the composition for retaining organs, tissues or cells is sufficient to enhance the viability or functions of organs, tissues or cells after grafting to the recipient.

The present invention relates to a method including: obtaining organs, tissues or cells from a donor; grafting the obtained organs, tissues or cells to a recipient; and administering the composition to the recipient. In the method, the amount of the active ingredient in the composition for retaining organs, tissues or cells is sufficient to enhance the viability or functions of organs, tissues or cells after grafting to the recipient. Here, the administration to the recipient can be continuously administered not only during or immediately after surgery but also during management after the operation.

The composition that contains, as an active ingredient, a peptide including the amino acid sequence represented by SEQ ID NO. 1, a fragment thereof, or a fusion peptide of the fragments; and contains, as an active ingredient, a fusion product including: a peptide consisting of the amino acid sequence represented by SEQ ID NO. 1, a fragment thereof, or a fusion peptide of the fragments; and a cell-penetrating peptide can be administered to both donors and recipients. In another aspect, the composition can be retained in the composition that is administered to a donor and/or recipient and that temporarily retains organs, tissues or cells during grafting.

The composition disclosed in this specification can be administered in such a manner that organs, tissues or cells are perfused in the body in the state in which organs, tissues or cells are present in the donor or recipient.

The organs, tissues or cells may be any organs, tissues or cells which can be grafted. For example, the organs can be liver, kidney, heart, pancreas, lung, small intestine and/or skin, and can be tissues or cells thereof.

The donor may be identical to or different from the recipient. Both the donor and the recipient can be non-human or human. Alternatively, the donor can be an animal, such as a pig, other than human, and the recipient can be human. In one embodiment, the tissues or cells may be the recipient's own tissues or cells. In other words, the donor and the recipient may be identical to each other.

The organs, tissues, cell masses and/or isolated cells can be extracted from the donor and grafted by any method known to those skilled in the art (see Oxford Textbook of Surgery, Morris and Malt, Eds., Oxford University Press (1994)). Those skilled in the art will appreciate that the extraction and grafting methods may vary depending on various circumstances such as the type of organs, tissues or cells, and the type of donor.

MODE FOR INVENTION

Hereinafter, the present invention will be described in more detail with reference to examples. However, the disclosure including the following examples should not be construed as confining or limiting the scope and content of the present invention. In addition, it is obvious that those skilled in the art can easily implement the present invention that does not specifically suggest experimental results so long as it is based on the disclosure including the following examples, and that these alterations and modifications fall within the scope of the claims.

<Test Method>

1) Cell Lines and Cell Culture

EL4 (mouse lymphoma T cell line) and Jurkat (human lymphoma T cell line) cells were purchased from the American Type Culture Collection (ATCC) and cultured using Roswell Park Memorial Institute (RPMI) 1640 media (Corning) with 10% fetal bovine serum (FBS; Corning) and 1% penicillin/streptomycin antibiotics (HyClone). HeLa cells (human cervical cancer cells) were purchased from the ATCC and cultured in Dulbecco's modified Eagle's media (DMEM) containing GlutaMAX supplemented with 10% fetal bovine serum (FBS) and 1% penicillin/streptomycin antibiotics. All the cells were stored at 37° C. in a 5% carbon dioxide incubator. All the aforementioned reagents were purchased from Thermo Scientific HyClone.

2) Animals

C.B-17 SCID/beige female mice and Rag1−/−IL-2rγ$^{null}$ (DKO) mice were used at about 8 weeks of age. All protocols involving animals were approved by the Yale Animal Care and Use committee. For skin graft experiments, the animals were housed individually in microisolator cages and fed autoclaved food and water. For HUVEC-collagen gel graft experiments, 4-5 animals were housed in microisolator cages and fed autoclaved food and water.

3) In Vitro Transfer Efficiency in Mouse Spleen Cells

Jurkat T-cells were cultured at a density of $5.0 \times 10^5$ cells/well on a 24-well plate in RPMI 1640 medium. After the cells were seeded, respective proteins were added at designated times. After culturing, the cells were collected and washed three times with phosphate buffered saline (PBS). Intracellular fluorescence was analyzed with a fluorescence-activated cell sorting (FACS) Canto II flow cytometer (BD Bioscience) and data were analyzed using FlowJo software (Tree Star, INC.). The spleen isolated from the 6-week-old C57BL/6 mice were loaded on a 60 mm×15 mm cell culture dish containing 3 ml of PBS. A single cell suspension was physically prepared using a cell strainer having pores with a size of 0.45 µm, 10 ml of fresh PBS was added thereto and the resulting mixture was centrifuged.

Erythrocyte cells were dissolved in an ACK buffer solution (0.15 M $NH_4Cl$, 10 mM $KHCO_3$, 1 mM EDTA-2Na, pH 7.2). After $1.0 \times 10^6$ spleen cells were seeded on each well, transfer efficiencies of the proteins according to the present invention were investigated. The cells were stained with anti-mouse CD4-PerCP-Cy5.5 and anti-mouse CD19-PE-Cy7 or anti-mouse F4/80 PerCP-Cy5.5, anti-mouse MHCII-PE, anti-mouse CD11b-PE-Cy7 and anti-mouse CD11c-APC FACS antibodies, to classify the cells into various types. The antibodies were purchased from eBioscience Ltd.

4) In Vitro Toxicity Analysis

The viability of cells was measured using Cell Counting Kit-8 based on aqueous tetrazolium-8 (CCK-8, Dojindo). $5.0 \times 10^3$ HeLa cells in total were seeded on a 96-well plate and treated with different concentrations of 10, 30, 50 or 100 µM of ctCTLA-4 proteins or PBS for 24 hours. After culturing, the cells were washed with PBS and further cultured in the CCK-8 solution for 2 hours. Subsequently, optical density was analyzed using a 450 nm plate reader (Bio-Rad).

5) Isolation of Human PBMC and In Vitro Transfer Efficiency of Respective ctCTLA-4 Proteins Human peripheral blood mononuclear cells (PBMCs) were obtained from healthy donors by leukapheresis under a protocol approved by the Institutional Review Board of Hanyang University or the Yale Human Investigation Committee. PBMCs were isolated by density gradient centrifugation using lymphocyte separation medium. The cells were stored in 10% DMSO in liquid nitrogen for further use, thawed, and washed before use. The isolated lymphocytes were seeded at $1.0 \times 10^6$ cells/well and transfer efficiency of respective ctCTLA-4 proteins was analyzed. The cells were further stained with anti-human CD4-PE-Cy7, anti-human CD19-APC, anti-human CD11b-PE-Cy7 or anti-human CD11c-APC FACS antibodies, all of which were purchased from eBioscience Ltd.

6) Bioimaging of Primary CD4+T-Cells

The 6 week-old C57BL/6 mice were euthanized, and CD4+ T-cells and lymph nodes were isolated from the spleen using a CD4+ T cell negative selection kit (StemCell Technologies, INC). The isolated CD4+ T-cells in the RPMI medium were seeded on an anti-CD44 antibody-coated glass cover slip equipped in a Chamlide chamber. Then, a protein solution was charged into the chamber and time-lapse imaging was initiated. DIC and GFP images were recorded at an interval of 5 minutes for 2 hours. The obtained time-lapse images were analyzed using MetaMorph or Image J software 1.48 v.

7) Transfer Mechanism of Proteins According to the Present Invention

The isolated spleen cells were cultured in the presence of respective ctCTLA-4 proteins at various temperatures (4° C., 25° C. or 37° C.) for one hour. Spleen cells or HeLa cells were pre-treated at 37° C. for 30 minutes with heparin (0, 10, 20 or 50 µg/ml), methyl-beta-cyclodextrin (0, 3, or 5 mM), chlorpromazine (0, 10 or 30 µM) or amiloride (0, 1, 2 or 5 mM) and then treated with respective ctCTLA-4 proteins, and additionally cultured at 37° C. for one hour with respective ctCTLA-4 proteins. All of the cells were treated with trypsin (Thermo Scientific HyClone) and washed with FACS buffer solution (PBS containing 10% FBS, 5% sodium azide and 1% EDTA). Heparin, MβCD, chlorpromazine and amiloride were purchased from Sigma-Aldrich Inc.

8) Bioimaging using Multiphoton Microscope

For in vivo multiphoton imaging of brains, male C57BL/6 mice (23 g-25 g) were subjected to surgical operation to introduce an observation window to the cranium. The animals were narcotized by isoflurane inhalation and kept at body temperature (37° C.-38° C.) using a homeothermic heating pad system controlled by a rectal probe. The isoflurane level was set to 3% in order to induce narcotization and maintained at 1.5% during the cranium window operation or multiphoton imaging. The animals were monitored in detail throughout the entire process in order to check physiological health of animals. All surgical processes were approved by the Institutional Animal Care and Use Committee (IACUC) of SungKyunKwan University. The animals were fixed on a stereotaxic frame (David Kopf Instruments, Tujunga, Calif.), and a circular cranium window with a diameter of 3 mm was created on the right hemisphere, which was based on ML of +2.5 mm, and AP of −1.5 mm. After craniotomy, a customized chamber plate (Narishige Inc., Tokyo, Japan) having a 5 mm observation hole was placed on an open craniotomy site and immobilized with dentinal resin. Then, the craniotomy window was filled with a sterilized artificial brain spinal cord liquid (125 mM NaCl, 2.5 mM KCl, 25 mM $NaHCO_3$, 1.25 mM $NaH_2PO_4$, 2 mM $CaCl_2$, 1 mM $MgSO_4$, 10 mM glucose, pH 7.4), and covered with a 7 mm cover slip.

The craniotomy window was sealed with a cyanoacrylic adhesive agent and the animals were loaded on a head-fixation device (MAG-1, Narishige INC.) for observation using a multiphoton microscope (TCS SP8 MP, Leica Microsystems CMS GmbH). Here, imaging was conducted using a 900 nm Ti:sapphire laser (Chameleon Vision II, Coherent INC.), and emitted fluorescence signals were detected through a 585/40 bandpass filter cube on a hybrid detector (HyD). In order to track transfer of carrier peptides to brain tissues, the carrier peptides were injected in an amount of 2.5 mg/animal through the caudal vein and 3D z-stack images were then obtained at an interval of 20 minutes for 2 hours. The size of imaged brain was 354.29× 354.29 µm² (1024×1024 pixel), which was obtained using a 25× water-immersion objective lens (N.A. 0.95). The imaging depth was about 450 to 500 µm from the brain surface and resolution was 1 µm. After imaging, the corresponding images were analyzed using LAS AF 3.2.0 (Leica Microsystems CMS GmbH) and Imaris 7.7.2 (Bitplane) software.

9) Human Skin Graft Model

SCID/beige mice were given two human skin grafts as previously described. In brief, human skin was obtained from cadaveric donors through the Yale University Skin Bank under a protocol approved by the Yale Human Investigations Committee. Next, 0.5-mm-thick sheets were divided into 1-cm² pieces, kept at 4° C. in RPMI 1640 medium (Corning), and fixed onto similarly sized defects on the dorsum of SCID/beige recipients using staples. After ~4 weeks, 2×10⁸ isolated human peripheral blood mononuclear cells from an allogeneic donor in 500 µl of PBS were transferred intraperitoneally. PBS or 50 µg of dNP2-ctCTLA-4 was injected intraperitoneally every other day for 2 weeks. On day 14, the blood was collected through cardiac puncture and skin grafts were harvested and prepared as paraffin or frozen blocks.

10) HUVEC-Collagen Gel Graft Model

DKO mice were given two HUVEC-collagen gel grafts as previously described. In brief, HUVECs were isolated by collagenase treatment of human umbilical veins under a protocol approved by the Yale Human Investigation Committee and cultured in Medium 199 containing 20% fetal calf serum (both from Thermo Fisher Scientific), 50 µg/mL EC growth supplement, 100 µg/mL porcine intestinal heparin, 2 mM l-glutamine, 100 U/mL penicillin, and 100 µg/mL streptomycin (Corning). HUVECs were transfected with retroviral vectors expressing the caspase-resistant form of Bcl-2 in the presence of polybrene daily for up to 3 days. After that, HUVECs (3×10⁶ cells) were suspended in 1 mL of a solution containing rat tail type 1 collagen (1.5 mg/mL; BD Biosciences), human plasma fibronectin (100 µg/mL; Sigma-Aldrich), 25 mM HEPES, 0.075% $NaHCO_3$ (both from HyClone), and 10% fetal calf serum in M199 on ice. The pH was adjusted to 7.5 by 0.1M NaOH. The cell suspension was pipetted into a 24-well plate and warmed to 37° C. for 15 min to allow for polymerization of the collagen. For implantation into DKO mice, the gels were harvested and bisected 24 h after gel formation. Each gel segment was implanted subcutaneously into a bluntly dissected abdominal wall of the mouse. The wound was closed with staples. After 11 days, the staples were removed and 3×10⁷ isolated human peripheral blood mononuclear cells from an allogeneic donor in 500 µl of PBS were transferred intraperitoneally. PBS or 50 µg of dNP2-ctCTLA-4 was injected intraperitoneally every other day for 3 weeks. At day 21, the blood was collected through cardiac puncture and HUVEC-collagen gel grafts were harvested and prepared as paraffin or frozen blocks.

11) Tissue Histology

The paraffin blocks were sectioned (5-µm-thick) for immunostaining. Anti-human CD45RO antibody was applied overnight at 4° C. The slides were incubated with biotinylated secondary antibody for 1 h and washed with PBS. Slides were then incubated for 1 h with ABC reagent and incubated with diaminobenzidine (DAB; Vector Lab., Inc.) peroxide substrate until the desired color developed, followed by hematoxylin staining. The slides were observed by bright field microscopy. To quantify tissue infiltration of lymphocytes, the number of human CD45RO T cells within the cross-section of the tissues (skin grafts or HUVEC-collagen gel grafts) was measured using Image J 1.50i software.

12) Immunofluorescence

The frozen blocks were sectioned (8-µm-thick) for immunostaining. PE-conjugated anti-human CD3, PE-conjugated anti-human CD8, and FITC-conjugated anti-human CD4 antibodies (all from BD Biosciences) were applied overnight at 4° C. The slides were washed and stained with DAPI to evaluate the nuclei. The slides were observed by fluorescence microscopy. To quantify tissue infiltration of CD4 or CD8 T cells, the number of marker-positive cells for each subset within the cross-section of the tissues was measured using Image J 1.50i software. To stain live HUVECs in the gel tissues, paraffin blocks were sectioned(5-µm-thick) and incubated with FITC-conjugated ULEX (Vector Lab., Inc.) overnight at 4° C. The slides were washed and stained with DAPI (Thermo Fisher Scientific) to evaluate the nuclei. The slides were observed by fluorescence microscopy.

13) Blood Cell Flow Cytometry

Collected blood samples from in vivo experiments were separated into serum and blood cells. The cells were washed with PBS and erythrocytes were lysed using Ack buffer. After erythrocyte lysis, the remaining lymphocytes were fixed using fixation buffer (BD Biosciences) overnight at 4° C. The cells were analyzed by flow cytometry after staining with a specific combination of fluorescently-labelled antibodies against CD45, CD4, CD8 (all from BD Biosciences), granzyme B, and Foxp3 (both from Thermo Fisher Scientific). For intracellular staining, a Foxp3 staining kit (Thermo Fisher Scientific) was used according to the manufacturer's instructions.

14) Luminex Assay

Collected serum samples from in vivo experiments were analyzed to quantify cytokine and chemokine expression. A 19-plex Luminex kit (R&D, Inc.) for analyzing the concentration of human IFN-γ, IL-17A, TNF-a, CCL2, CCL3, CCL4, CXCL9, CXCL10, CXCL11, IL-1ra, IL-1β, IL-1a, GM-CSF, VEGF, and Osteopontin, was designed and used according to the manufacturer's instructions. The samples were analyzed with a Bioplex 2000 (Bio-Rad).

15) PBMC or T cell Functional Analysis In Vitro 2.5×10⁵ isolated human PBMCs per well were incubated in a 96-well round bottom plate. The wells were coated with anti-CD3 and anti-CD28 monoclonal antibodies (both from BD Biosciences) for 5 h at 37° C. PBS, dNP2-EGFP, or dNP2-ctCTLA-4 proteins were added to the culture medium at the start of cell incubation in all in vitro experiments. To analyze CD25 and CD69 expression, the cells were harvested after 12 h and washed with PBS. The activation markers were analyzed by flow cytometry after anti-CD4, anti-CD8, anti-CD25, and anti-CD69 antibody staining (all from BD Biosciences). To analyze CXCR3 expression, the cells were harvested after 48 h and stained with anti-CXCR3 antibody (BD Biosciences).

Next, human CD4*+ T cells or CD8*+ T cells were isolated from total PBMCs by magnetic-activated cell sorting (MACS; Miltenyi Biotec) according to the manufacturer's instructions. The sorted cells were labelled with eFluor 670 cell proliferation dye (Thermo Fisher Scientific). Next, 2.5×10⁵ labelled cells were incubated with plate-bound anti-CD3 and anti-CD28 monoclonal antibodies for 5 days at 37° C. The proliferating cells were analyzed by flow cytometry and the supernatants were analyzed with IFN-γ, TNF-a, and IL-17A ELISA kits (all from Biolegend). CD8 T cells were stimulated with plate-bound anti-CD3 and anti-CD28 monoclonal antibodies (both from BD Biosciences) for 5 days at 37° C. Functional activity of CD8 T cells was analyzed by flow cytometry after anti-CD8 (BD Biosciences) and anti-granzyme B (Thermo Fisher Scientific) intracellular antibody staining using a Foxp3 staining kit (Thermo Fisher Scientific).

16) Statistics

Data were analyzed using one-, or two-way ANOVA with multiple comparison tests or two-tailed Student's t-tests. P-values <0.05 were considered significant. Statistical analysis was performed using Prism 6 (GraphPad Software, Inc.).

PRODUCTION EXAMPLE 1

Synthesis/Separate Purification of Peptides, Fragments thereof and Fusion Peptides Peptides having amino acid sequences represented by Sequence ID Nos. 1 to 4 and 8 to 10 were synthesized.

At this time, the peptide having an amino acid sequence represented by Sequence ID No. 1 (hereinafter also referred to as "ctCTLA-4"), the peptide fragment having an amino acid sequence represented by Sequence ID No. 2 (hereinafter also referred to as "ctCTLA-4-fm1"), the peptide fragment having an amino acid sequence represented by Sequence ID No. 3 (hereinafter also referred to as "ctCTLA-4-fm2"), the fusion peptide having an amino acid sequence represented by Sequence ID No. 4 (hereinafter also referred to as "ctCTLA-4-fm3"), the cell-penetrating peptide having an amino acid sequence represented by Sequence ID No. (hereinafter also referred to as "dNP2"), the cell-penetrating peptide having an amino acid sequence represented by Sequence ID No. 9 (hereinafter also referred to as "Hph-1"), and the cell-penetrating peptide having an amino acid sequence represented by Sequence ID No. 10 (hereinafter also referred to as "TAT") were designated.

Sense and antisense oligodeoxynucleotides suitable for the amino acid sequences were each synthesized and then allowed to stand at 95° C. for 3 minutes to remove the resulting secondary or tertiary structures (denaturation) and DNA double strands were created at different temperatures of 50° C. and then 72° C. For insertion into pRSET-b vectors, sequences specific to restriction enzymes, apart from the sense and antisense oligodeoxynucleotides, were introduced into 5' and 3'. Then, the sequences were amplified in bulk in *Escherichia*. Then, the integrity of sequences was identified and the sequences were transferred into *Escherichia* to induce expression. Respective peptides expressed from the respective strains were purified.

PRODUCTION EXAMPLE 2

Synthesis/Separate Purification of Peptide Variants

Peptides having amino acid sequences represented by Sequence ID Nos. 5 to 7 were synthesized. Peptide variants having Sequence ID Nos. 5 to 7 were obtained by substituting, by F, Y amino acid residues of "1Y" and "2Y" shown in FIG. 1A in the Sequence ID No. 1.

Specifically, the peptide variant having an amino acid sequence represented by Sequence ID No. 5 was obtained by substituting, by F, the Y amino acid residue of the part represented by "1Y", which is represented by "1YF", the peptide variant having an amino acid sequence represented by Sequence ID No. 6 was obtained by substituting, by F, the Y amino acid residue of the part represented by "2Y", which is represented by "2YF", and the peptide variant having an amino acid sequence represented by Sequence ID No. 7 was obtained by substituting, by F, the Y amino acid residues of both "1Y" and "2Y" parts, which is represented by "DYF".

Peptide variants were synthesized and separately purified in the same manner as in Production Example 1 except that the amino acid sequences were used.

PRODUCTION EXAMPLE 3

Production of Fusion Products (dNP2-ctCTLA-4, Hph-1-ctCTLA-4, TAT-ctCTLA-4)

In order to fuse the peptide having an amino acid sequence represented by Sequence ID No. 1 produced in Production Example 1 with the cell-penetrating peptide, a primer for linking the cell-penetrating peptide represented by Sequence ID No. 8, Sequence ID No. 9, or Sequence ID No. 10 to the N-end of ctCTLA-4 peptide was produced to produce dNP2-ctCTLA-4, Hph-1-ctCTLA-4 or TAT-ctCTLA-4 genes through PCR reaction, these genes were injected into vectors (pRSET-b) to express proteins in *Escherichia* strains, the proteins were purified, and testing to confirm transfer efficiency of the proteins into cells was conducted. The detailed procedure will be described below.

1) Production of Encoding Genes

The DNA base sequence for encoding the cell-penetrating peptide having an amino acid sequence represented by Sequence ID No. 8, Sequence ID No. 9 or Sequence ID No. 10 was added to the DNA base sequence for encoding a part of the N-end of the peptide having an amino acid sequence represented by Sequence ID No. 1 obtained in Production Example 1 to produce forward primers. Respective primers, Sequence ID Numbers and restriction enzyme recognition sites are briefly shown in Table 1.

PCR reaction was conducted using, as a template, the pRSETb vector containing the gene for encoding the peptide Sequence ID No. 1 with primers represented by Sequence ID Nos. 21 to 24.

30 cycles were conducted using a PCR reactor (Biorad) and each cycle included initial thermal denaturation reaction at 95° C. for 3 minutes, thermal denaturation reaction of the template at 95° C. for 20 seconds, polymerization reaction for linking the primer to the template at 50° C. for 20 seconds, and elongation reaction at 72° C. for 30 seconds.

TABLE 1

| No. | Primer | Base Sequence |
|---|---|---|
| Seq. ID No. 21 | Primary forward primer of dNP2-ctCTLA-4 | AAGATTAAGAAAGTCAAGAAGAAAGGAAGAA AGGAATTCTACCCATACGATGTTCCAGATTA CGCTA |
| Seq. ID No. 22 | Secondary forward primer of dNP2-ctCTLA-4 | GCTAGCAAGATTAAGAAAGTCAAGAAGAAAG GAAGAAAGGGATCCAAGATTAAGAAAGTCAA GAAGA |
| Seq. ID No. 23 | Forward primer of TAT-ctCTLA-4 | GCTAGCTATGGACGCAAGAAGCGCCGCCAGC GCCGCCGCGGATCCTACCCATACGATGTTCC AGATTACGCTA |
| Seq. ID No. 24 | Primer of Hph-1-ctCTLA-4 | TATGCGCGTGTGCGACGTCGTGGCCCACGTC GAGGATCCTACCCATACGATGTTCCAGATTA CGCTA |

Meanwhile, among the forward primers, the dNP2-ctCTLA-4 was divided into two portions for PCR reaction because of very long sequence of dNP2 (KIKKVKKKGRKGSKIKKVKKKGRK).

2) Production of Recombinant Expression Vectors

In order to express dNP2-ctCTLA-4, Hph-1-ctCTLA-4 or TAT-ctCTLA-4 fusion products, the gene (DNA) fragment produced in 1) of Production Example 3 was cut with a restriction enzyme and then inserted into the protein-expressing vector, pRSETb, using a ligase.

The DNA fragment amplified in 1) of Production Example 3 was subjected to enzyme reaction using NheI and HindIII (NEB) such that the 5'/3' ends of the DNA became sticky ends. Meanwhile, pRSETb was subjected to enzyme reaction using two identical restriction enzymes to produce linear pRSETb vectors having NheI and HindIII insertion sites. After respective enzyme reactions, isolation was conducted using a PCR purification kit (Cosmogenetech Co., Ltd.).

The isolated dNP2-ctCTLA-4, Hph-1-ctCTLA-4 or TAT-ctCTLA-4 fusion product double-chain DNA fragments were connected to the pRSET-b vectors at 25° C. for two hours by enzyme reaction using a T4 ligase (NEB).

The connected circular pRSETb vectors into which dNP2-ctCTLA-4, Hph-1-ctCTLA-4 or TAT-ctCTLA-4 thus was inserted were transformed into DH5α Escherichia strains and cultured in LB plate medium containing 50 μg/ml of ampicillin as an antibiotic to select transformed Escherichia for forming colonies. The selected Escherichia colonies were cultured in a liquid medium (LB) containing 50 μg/ml of ampicillin again and plasmid vectors were then isolated using a plasmid mini preparation kit (Cosmogenetech Co., Ltd.).

In order to identify that the plasmid vector isolated through the process was the pRSETb vector into which the dNP2-ctCTLA-4, Hph-1-ctCTLA-4 or TAT-ctCTLA-4 was inserted, enzyme reaction was primarily conducted using NheI and HindIII restriction enzymes, and DNA base sequence analysis (Bionics) was then finally conducted.

3) Isolation and Purification of Proteins

The pRSETb vector, into which dNP2-ctCTLA-4, Hph-1-ctCTLA-4, TAT-ctCTLA-4 or dNP2-ctCTLA-4-fm3 was inserted, produced in 2) of the Production Example 3, was transformed into Escherichia BL21 (DE3) Star pLysS strains, colonies created in an LB plate medium containing 34 μg/ml of chloramphenicol and 50 μg/ml of ampicillin as antibiotics were seeded into 50 ml of a liquid LB medium and cultured at 37° C. for 10 hours, and the resulting culture solution was seeded onto 500 mL of a fresh LB liquid medium. The solution was cultured until the amount of Escherichia corresponded to O.D. of 0.5 when the culture solution was measured at the same temperature, isopropyl β-D-1-thiogalactopyranoside (IPTG) was added at a concentration of 1 mM and further cultured in a shaking incubator having a temperature of 20° C. and a constant rotation rate of 150 rpm for 14 hours. The proteins expressing Escherichia strains included a 6X-His tag encoded in pRSET-b vectors at a front side thereof. The proteins were purified using this by the following testing method.

The culture solution was collected by centrifugation and then re-suspended in a native lysis solution (0.5M NaCl, 5 mM imidazole, 20 mM Tris-HCl, pH 8.0). In order to disrupt Escherichia cell walls and cell membranes, the suspension in the lysis solution was allowed to stand for 10 minutes. In addition, the cells were broken using an ultrasonic cell disrupter VCX-130 (Sonics & Materials) and centrifuged to isolate the supernatant. The isolated supernatant was filtered once using a 0.45 μm filter (Advantec) and then bonded to Ni-NTA agarose (Qiagen) at room temperature for 1 hour. Then, only the Ni-NTA agarose-bonded protein product was bound to the column using a histidine column (His-column, Biorad). The column was washed with 20 mM and 250 mM imidazole solutions and finally eluted using a 3M imidazole solution. The eluted protein product was applied to the PD-10 Sephadex G-25 column (GE Healthcare Life Sciences) for desalination to isolate and purify the dNP2-ctCTLA-4, Hph-1-ctCTLA-4 or TAT-ctCTLA-4 fusion product.

To obtain highly purified proteins, an additional ion-exchange protein purification step was performed using SP Sepharose High Performance (GE Healthcare Life Sciences), followed by desalting on a PD-10 Sephadex G-25 column. Proteins were stored at −80° C. and the concentrations were measured using the Bradford solution (Bio-Rad) right before the experiments.

Figure 2:
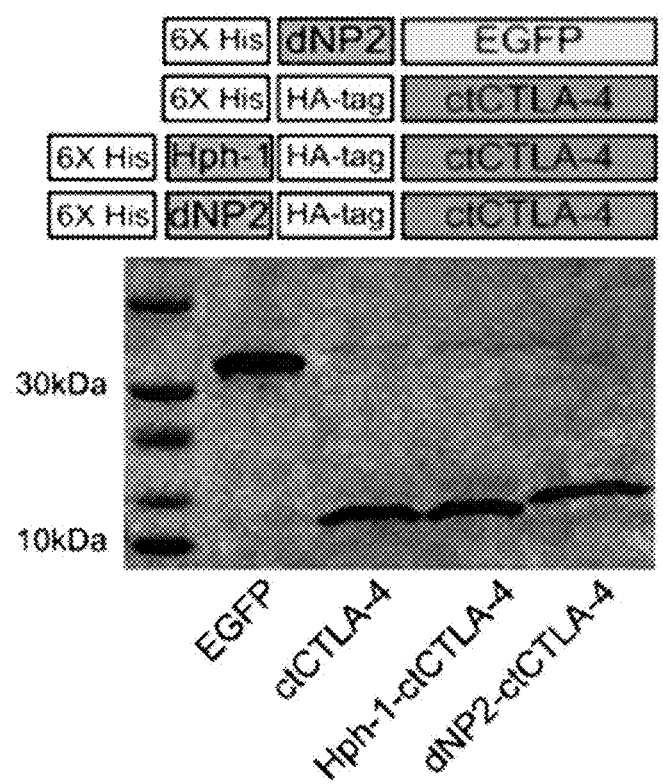
FIG. 2 shows the structure of a dNP2-ctCTLA-4 fusion protein according to the present invention and analysis results of the dNP2-ctCTLA-4 fusion protein using SDS-PAGE.

A part of the purified protein was identified through 12% SDS-PAGE and is shown in FIG. 2.

PRODUCTION EXAMPLE 4

Production of dNP2-ctCTLA-4-fm3 Fusion Product

The fusion product (hereinafter also referred to as "dNP2-ctCTLA-4-fm3 fusion product") including the fusion peptide (hereinafter also referred to as "ctCTLA-4-fm3") having an amino acid sequence represented by Sequence ID No. 4, produced in Production Example 1, and the cell-penetrating peptide (dNP2) having an amino acid sequence represented by Sequence ID No. 8 was synthesized by Cosmogenetech Co., Ltd.

PRODUCTION EXAMPLE 5

Synthesis and Separate Purification of Control Group (dNP2-EGFP)

In order to fuse the cell-penetrating peptide having an amino acid sequence represented by Sequence ID No. 8 produced in Production Example 1 with a green florescent protein (EGFP), primers for binding EGFP to the N-end of dNP2 were produced, dNP2-EGFP genes were produced through PCR reaction and inserted into vectors (pRSET-b), and proteins were expressed in Escherichia strains and purified. The overall process was the same as in Production Example 3, except for the primers. The primers used are as follows.

```
Primary forward primer
                                  [Sequence ID No. 25]
AAGATTAAGAAAGTCAAGAAGAAAGGAAGAAAGGTGAGCAAGGGCGAGGAG

CTGTTCACCG

Secondary forward primer
                                  [Sequence ID No. 26]
GCTAGCAAGATTAAGAAAGTCAAGAAGAAAGGAAGAAAGGGATCCAAGATT

AAGAAAGTCAAGAAGA
```

PRODUCTION EXAMPLE 6

Synthesis of Control Group (dNP2-TAMRA)

In order to produce a fusion product of the cell-penetrating peptide having an amino acid sequence represented by Sequence ID No. 8 produced in Production Example 1, with a florescent labelling compound, TARMA, the substance synthesized by Cosmogenetech Co., Ltd. was used.

PRODUCTION EXAMPLE 7

Synthesis of Control Group (TAT-EGFP)

In order to produce a fusion product of the cell-penetrating peptide (dNP2) represented by Sequence ID No. 8 produced in Production Example 1, with a green florescent protein (EGFP), the substance synthesized by Cosmogenetech Co., Ltd. was used.

TEST EXAMPLE 1

1) Comparison of Transfer Efficiency of dNP2 in Primary Human T Cells

The cell-penetrating peptide (dNP2) of SEQ ID NO. 8 obtained from Preparation Example 1 is known to have higher protein transfer efficiency into cells than other cell-penetrating peptides (CPP). Therefore, in the present Test Example, cell-penetrating peptides with the highest protein transfer efficiency for primary human T cells were identified. Specifically, dNP2-EGFP, TAT-EGFP, and EGFP proteins were administered to both murine and human cells at a concentration of 5 µM, and delivery efficiency thereof was evaluated.

FIGS. 3A to 3D show results of flow cytometry regarding all cells, after culturing EL4 cells (a-b), mouse spleen cells (a-b), Jurkat cells (c-d) and human peripheral blood mononuclear cells (PBMCs) (c-d) in the presence of 5 µM of EGFP, TAT-EGFP, dNP2-EGFP or PBS, and after 1 hour, staining mouse spleen cells and human PBMCs with anti-mouse CD4 or anti-human CD4 fluorescent-labeled antibodies.

Figure 3A:
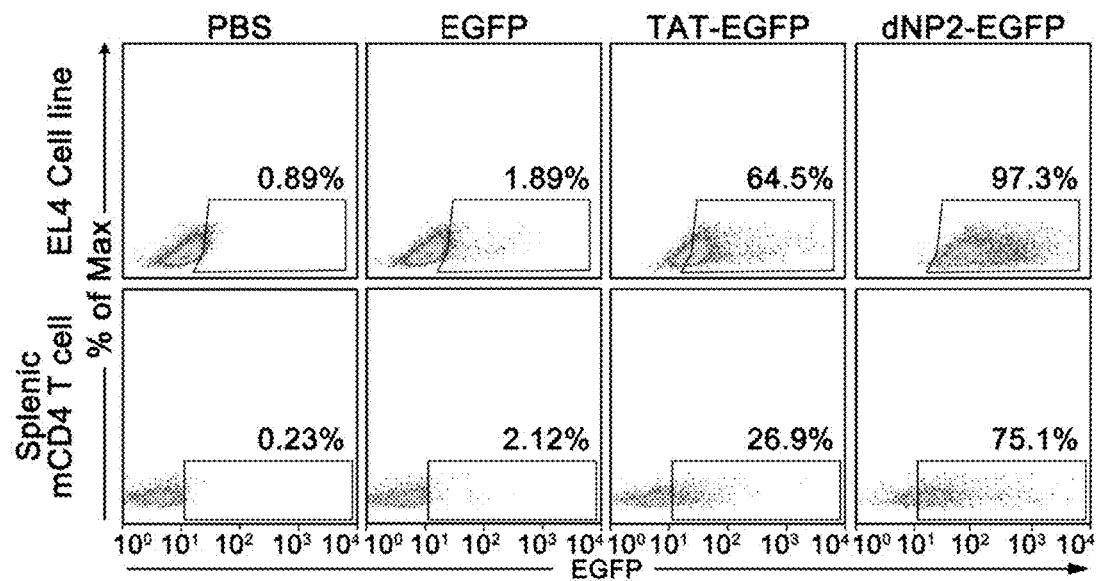
FIGS. 3A to 3D show results of flow cytometry regarding all cells, after culturing EL4 cells (a-b), mouse spleen cells (a-b), Jurkat cells (c-d) and human peripheral blood mononuclear cells (PBMCs) (c-d) in the presence of 5 µM of EGFP, TAT-EGFP, dNP2-EGFP or PBS, and after 1 hour, staining mouse spleen cells and human PBMCs with anti-mouse CD4 or anti-human CD4 fluorescent-labeled antibodies.
Figure 3B:
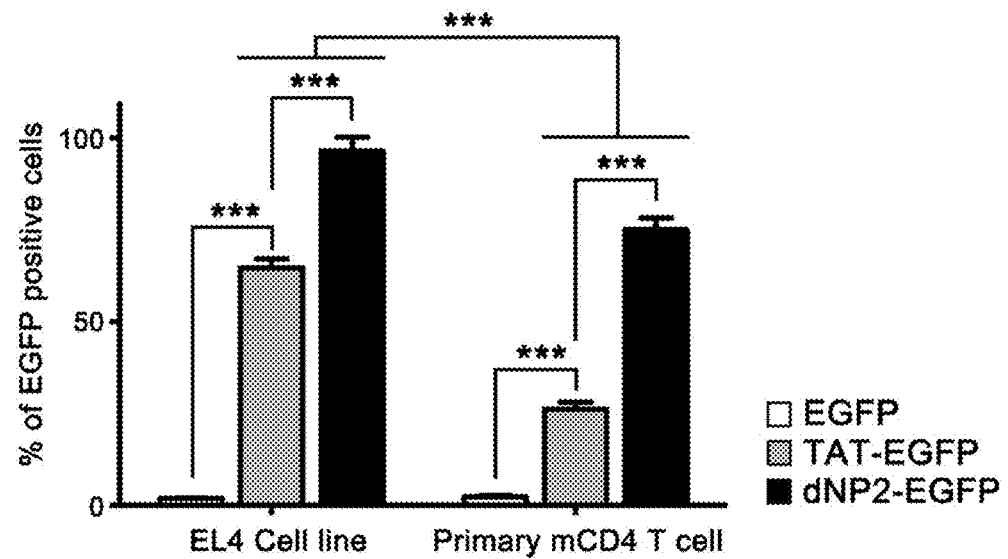
Figure 3C:
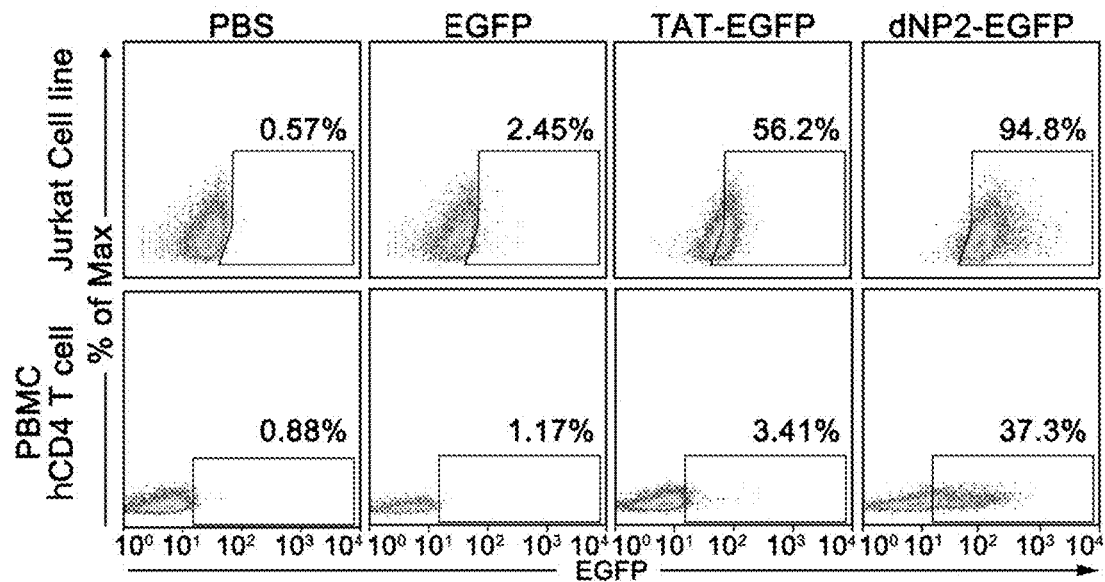
Figure 3D:
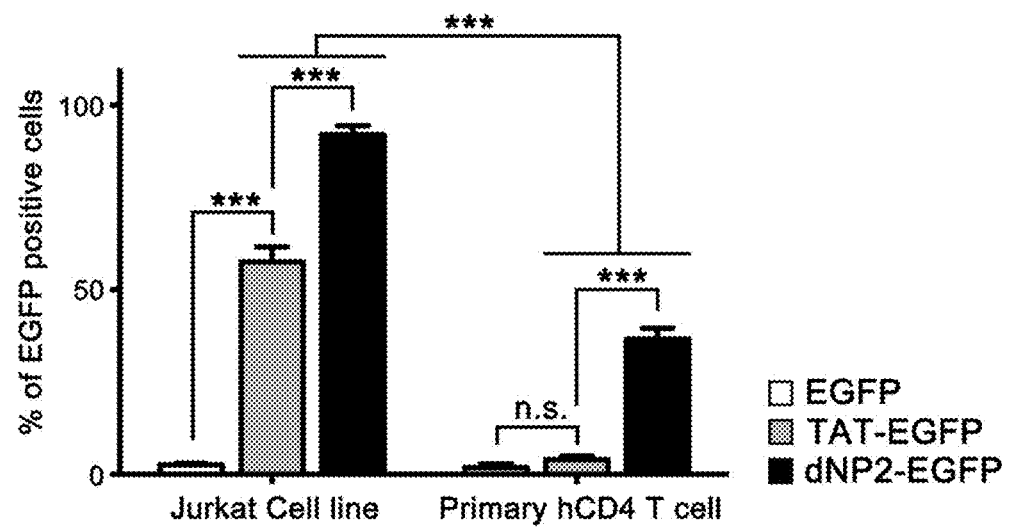
Figure 3E:
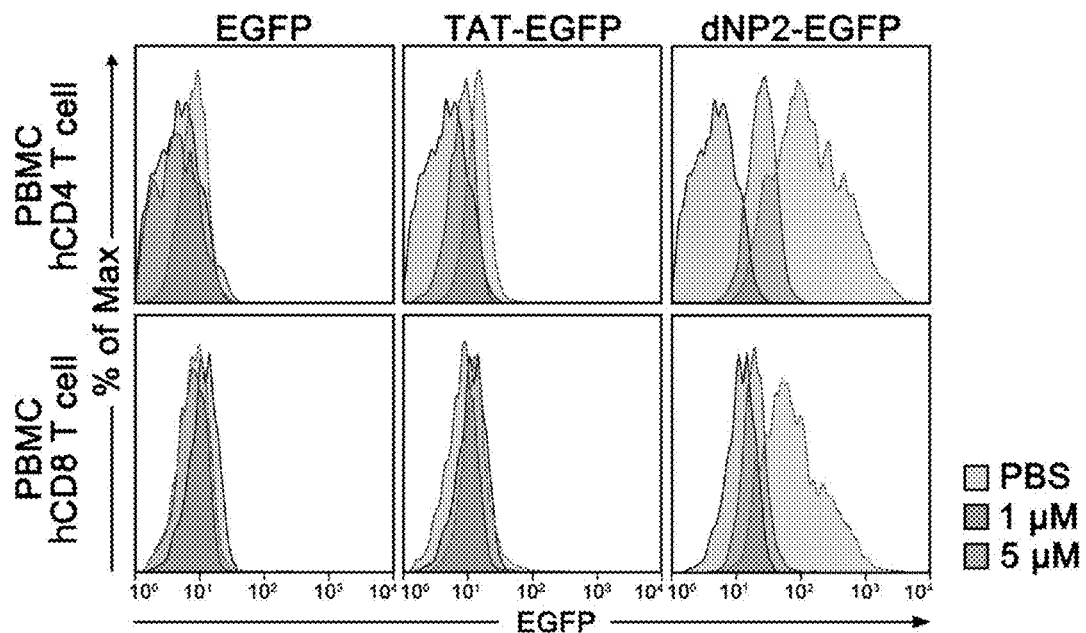
FIGS. 3E to 3F show results of flow cytometry regarding all cells, after administering PBS, 1 or 5 µM of EGFP, TAT-EGFP or dNP2-EGFP to human PBMCs and staining with anti-human CD4 and anti-human CD8 fluorescent-labeled antibodies, In FIG. 3, the bar graphs are shown as mean±standard deviation.
Figure 3F:
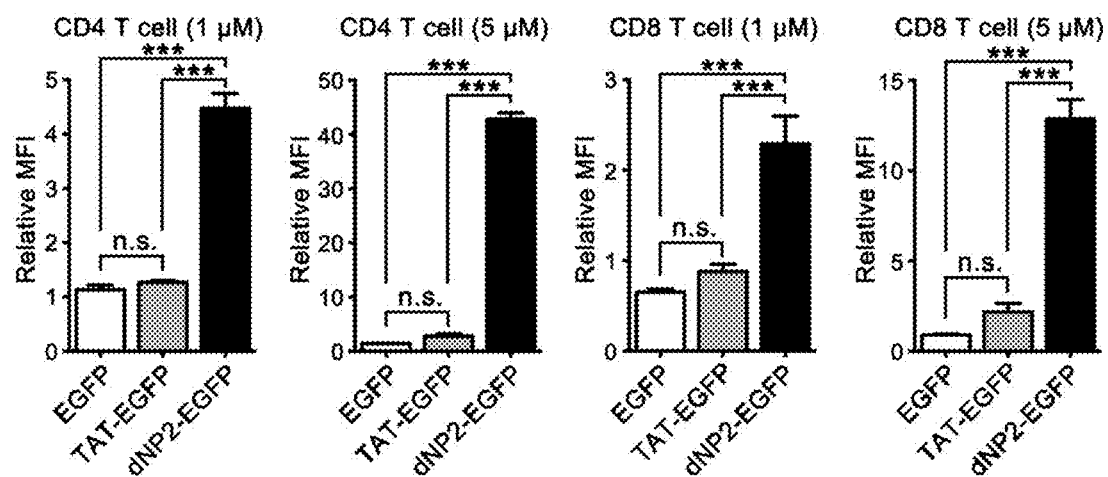

FIGS. 3E to 3F show results of flow cytometry regarding all cells, after administering PBS, 1 or 5 µM of EGFP, TAT-EGFP or dNP2-EGFP to human PBMCs and staining with anti-human CD4 and anti-human CD8 fluorescent-labeled antibodies. In FIG. 3, the bar graphs are shown as mean±standard deviation, FIGS. 3B and 3D are shown using bi-directional ANOVA for statistical analysis, ***means $p<0.001$, and n.s is an insignificant number.

As shown in FIG. 3, dNP2-EGFP transmits proteins to primary human T cells with higher efficiency than TAT-EGFP. Specifically, as shown in FIGS. 3A and 3B, dNP2-EGFP showed significantly higher intracellular protein transfer efficiencies at higher efficiency than TAT-EGFP in spleen CD4 T cells. The efficiency of dNP2-EGFP in EL4 cancer cells was significantly higher than in primary cells.

As can be seen from FIGS. 3C and 3D, similar patterns were observed in human peripheral CD4 T cells and Jurkat cells. It could be seen that dNP2 cell-penetrating peptide based on poly-arginine was firstly delivered to cancer cells. Protein transfer efficiency of TAT-EGFP was higher in human CD4 T cells than in the control group, but the difference therebetween was not significant. In contrast, dNP2-EGFP showed significantly higher protein transfer efficiency in human CD4 T cells than in the control group, which suggests that dNP2-EGFP is more preferable to human T cells than TAT-EGFP. In addition, the capacity-dependency of various concentrations (0.1-20 µM) of proteins in human PBMCs was evaluated. As a result, it was further confirmed that dNP2-EGFP had a significantly higher protein transfer efficiency than TAT-EGFP at all doses.

As can be seen from FIGS. 3E and 3F, when the concentration of dNP2-EGFP was 1 µM, it was 13.8 times higher than that of CD4 cells and 5.323 times higher than that of CD8 at 5 µM. In addition, cytotoxicity of PBMCs treated with various concentrations of dNP2-EGFP and TAT-EGFP (0.1-20 µM) was analyzed and, as a result, no significant cytotoxicity was observed. These results demonstrate that dNP2-based protein transfer to human T cells is an efficient way to control human T cell functions.

2) Comparison in Transfer Efficiencies between ctCTLA-Peptides, and dNP2-ctCTLA-4 and Hph-1-ctCTLA-4 Fusion products into mouse spleen cells (immune cells)

The intracellular introduction efficiency was compared between the ctCTLA-4 peptide purified in Production Example 1, and dNP2-ctCTLA-4 and Hph-1-ctCTLA-4 fusion products purified in Production Example 3.

Specifically, the transfer efficiency was measured using "3) In vitro transfer efficiency" in the test method, which will be briefly described below.

Mouse spleen cells were cultured together with 1 µM of a ctCTLA-4 peptide, or a dNP2-ctCTLA-4 or Hph-1-ctCTLA-4 fusion product for one hour, and the ctCTLA-4 peptide or CPP-linked ctCTLA-4 fusion products, which had been transferred into cells, were stained with anti-HA antibodies. Signals were amplified with PE-conjugated anti-rabbit IgG antibodies. The cells were harvested and intracellular fluorescence was measured using a flow cytometer to measure ctCTLA-4 protein introduction efficiency in primary mouse CD4-T-cells.

Figure 4:
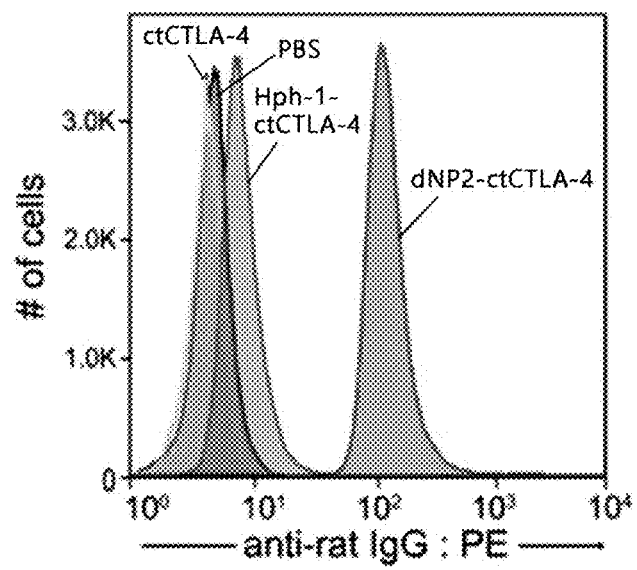
FIG. 4 is a graph showing intracellular transfer efficiencies of the ctCTLA-4 peptide, and dNP2-ctCTLA-4 and Hph-1-ctCTLA-4 fusion products in primary mouse CD4-T-cells.

FIG. 4 is a graph showing intracellular transfer efficiencies of the ctCTLA-4 peptide, and dNP2-ctCTLA-4 and Hph-1-ctCTLA-4 fusion products in primary mouse CD4-T-cells.

As shown in FIG. 4, 1 µM of the ctCTLA-4 peptide exhibited excellent intracellular transfer efficiency even though it was not linked to the cell-penetrating peptide (hereinafter also referred to as "CPP").

It could be seen that, when the CPP was linked to the ctCTLA-4 peptide, intracellular transfer efficiency of (dNP2-ctCTLA-4 or Hph-1-ctCTLA-4 fusion product) was further improved, preferably, the dNP2-ctCTLA-4 fusion product exhibited the highest intracellular transfer efficiency. Specifically, the dNP2-ctCTLA-4 fusion product exhibited about at least 10 times higher intracellular transfer efficiency than the Hph-1-ctCTLA-4 fusion product and the ctCTLA-4 peptide.

Through the test, the dNP2-ctCTLA-4 fusion product having the best transfer efficiency was screened from the fusion products wherein CPP was fused to ctCTLA-4, and in the following test, comparison and analysis were conducted based on the dNP2-ctCTLA-4 fusion product produced using dNP2, which is representative of conventional CPPs.

TEST EXAMPLE 2

Analysis of Cytokine Expression of dNP2-ctCTLA-4 in Spleen Cells

Figure 5:
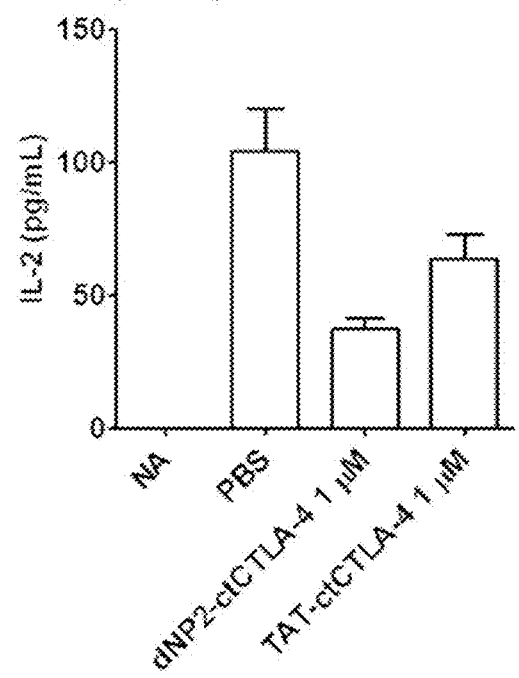
FIG. 5 is a graph showing IL-2 expression inhibitory efficiency of 1 µM PBS, the dNP2-ctCTLA-4 fusion product and the TAT-ctCTLA-4 fusion product. The numbers represent mean±standard deviation, represents $p<0.05$, represents $p<0.01$, and *represents $p<0.001$; Student's t-test.

1) Evaluation of IL-2 Expression Inhibitory Ability of CPP-ctCTLA-4 Fusion Product Depending on type of CPP The spleen cells activated by anti-CD3 and anti-CD28 antibodies were treated with 1 µM of each of PBS, the dNP2-ctCTLA-4 fusion product and the TAT-ctCTLA-4 fusion product, and IL-2 expression inhibitory efficiency was measured by ELISA and shown in FIG. 5.

First, a 96-well plate was coated at a concentration of 0.1 µg/well with anti-CD3 (anti-mouse CD3) and anti-CD28 (anti-mouse CD28) monoclonal antibodies at 37° C. for 5 hours, spleen cells were isolated from 7-week-old C57BL/6, and the isolated spleen cells were suspended to be single cells. The spleen cells suspended through the process were seeded at $2.5 \times 10^5$ on each well coated with anti-CD3 (anti-mouse CD3) and anti-28 (anti-mouse CD28) monoclonal antibodies, and were treated with 1 µM PBS, the dNP2-ctCTLA-4 fusion product and the TAT-ctCTLA-4 fusion product, and then activated for 24 hours.

FIG. 5 is a graph showing IL-2 expression inhibitory efficiency of 1 µM PBS, the dNP2-ctCTLA-4 fusion product and the TAT-ctCTLA-4 fusion product. The numbers represent mean±standard deviation, represents $p<0.05$, represents $p<0.01$, and *represents $p<0.001$; Student's t-test.

As can be seen from FIG. 5, the ctCTLA-4 protein according to the present invention exhibited a 40% to 70% decrease in IL-2 expression through linkage with the conventional cell-penetrating peptide (TAT, dNP2, Hph-1), compared to the counterpart subjected to PBS treatment. It could be seen that, thereamong, the dNP2-ctCTLA-4 fusion product exhibited the best decrease effect of 70% (specifically, at least two times higher effect than the TAT-ctCTLA-4 fusion product).

2) Evaluation of IL-2 Expression Inhibitory Ability of ctCTLA-4

IL-2 expression inhibitory ability was compared between the dNP2-ctCTLA-4 fusion product purified in Production Example 3 and the dNP2-EGFP fusion product (control group) purified in Production Example 5.

Figure 6A:
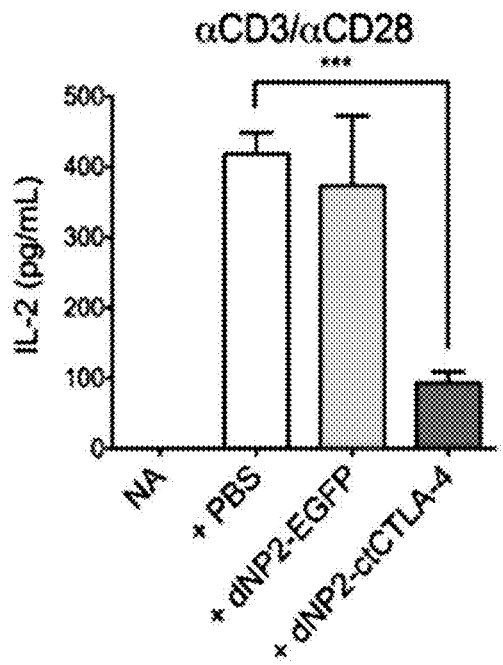
FIGS. 6A and 6B are graphs showing IL-2 expression inhibitory efficiency of the dNP2-ctCTLA-4 fusion product and the dNP2-EGFP fusion product. The numbers represent mean±standard deviation, represents $p<0.05$, represents $p<0.01$, and *represents $p<0.001$; Student's t-test.

The spleen cells activated by the anti-CD3 and anti-CD28 antibodies were each treated with the dNP2-ctCTLA-4 fusion product and the dNP2-EGFP fusion product, and IL-2 expression inhibitory efficiency was measured by ELISA and shown in FIG. 6A. At this time, ELISA was conducted using the kit produced by Biolegend Corporation in accordance with the standard protocol provided by the manufacturer. In addition, spleen cells activated by PMA/ionomycin were treated with the dNP2-ctCTLA-4 fusion product and the dNP2-EGFP fusion product, and IL-2 expression inhibitory efficiency was measured by ELISA and is shown in FIG. 6B.

At this time, the activated spleen cells were activated with the anti-CD3/CD28 antibody or PMA/ionomycin in the presence of 1 μM PBS, the dNP2-ctCTLA-4 fusion product or dNP2-EGFP fusion product for 24 hours.

Figure 6B:
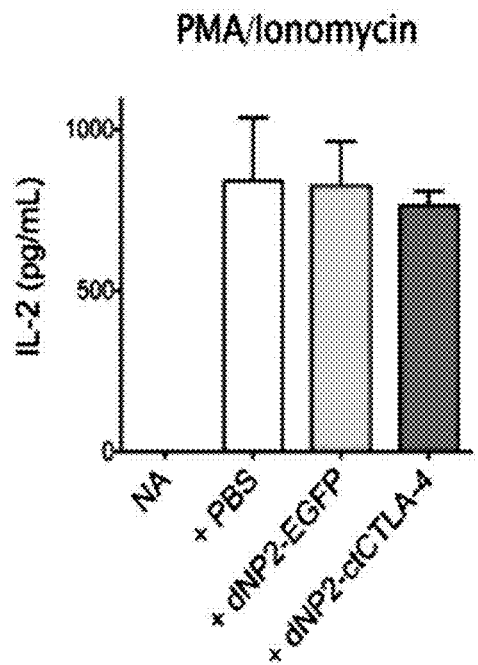

FIGS. 6A and 6B are graphs showing IL-2 expression inhibitory efficiency of the dNP2-ctCTLA-4 fusion product and the dNP2-EGFP fusion product. The numbers represent mean±standard deviation, represents $p<0.05$, represents $p<0.01$, and *represents $p<0.001$; Student's t-test.

As can be seen from FIG. 6, the dNP2-ctCTLA-4 fusion product inhibited IL-2 expression, while the dNP2-EGFP fusion product could not inhibit IL-2 expression. Furthermore, the dNP2-ctCTLA-4 fusion product according to the present invention did not have any effect on the spleen cells activated by stimulation of PMA and ionomycin, which demonstrates that the target of the dNP2-ctCTLA-4 fusion product was adjacent TcR signal molecules. That is, it can be seen that the dNP2-ctCTLA-4 fusion product according to the present invention had a specific-target directivity. Accordingly, it can be seen the IL-2 expression inhibitory effect was due to ctCTLA-4, not dNP2.

3) Evaluation of IFN-γ and IL-17A Expression Inhibitory Ability of ctCTLA-4

IFN-γ and IL-17A expression inhibitory abilities were compared between the dNP2-ctCTLA-4 fusion product purified in Production Example 3 and the dNP2-EGFP fusion product (Control group) purified in Production Example 5.

The spleen cells activated by the anti-CD3 and anti-CD28 antibodies were each treated with the dNP2-ctCTLA-4 fusion product and the dNP2-EGFP fusion product, and IFN-γ and IL-17A expression inhibitory abilities were measured by ELISA and are shown in FIG. 7.

Figure 7A:
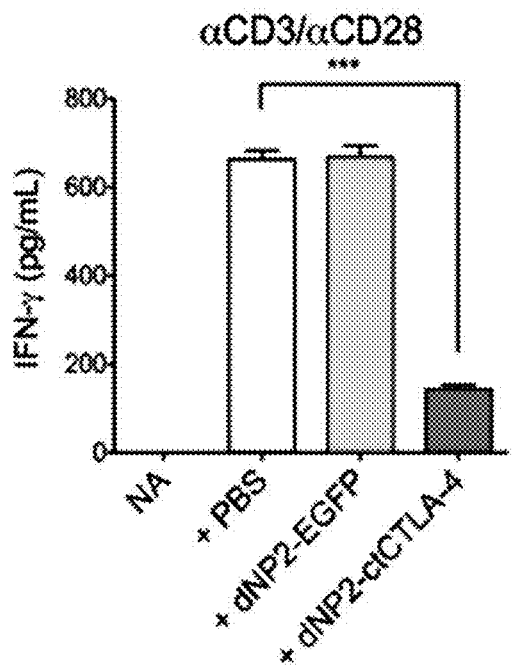
FIG. 7A is a graph showing IFN-γ expression inhibitory efficiency of the dNP2-ctCTLA-4 fusion product and the dNP2-EGFP fusion product and FIG. 7B is a graph showing IL-17A expression inhibitory efficiency of the dNP2-ctCTLA-4 fusion product and the dNP2-EGFP fusion product. The numbers represent mean±standard deviation, represents $p<0.05$,  represents $p<0.01$, and *represents $p<0.001$; Student's t-test.
Figure 7B:
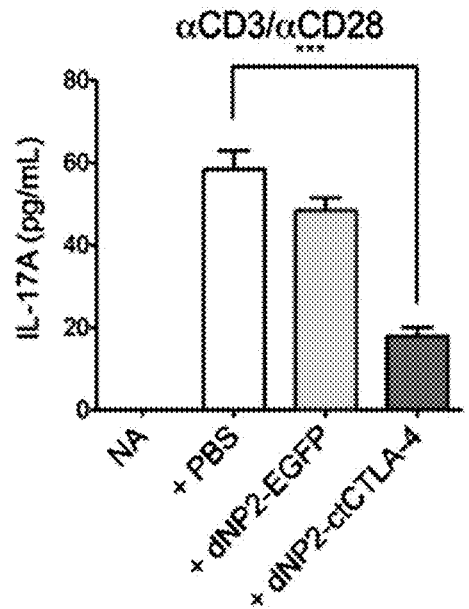

FIG. 7A is a graph showing IFN-γ expression inhibitory efficiency of the dNP2-ctCTLA-4 fusion product and the dNP2-EGFP fusion product and FIG. 7B is a graph showing IL-17A expression inhibitory efficiency of the dNP2-ctCTLA-4 fusion product and the dNP2-EGFP fusion product. The numbers represent mean±standard deviation, represents $p<0.05$,  represents $p<0.01$, and *represents $p<0.001$; Student's t-test.

As can be seen from FIG. 7, levels of interferon-γ (IFN-γ) and interleukin-17A (IL-17A) expressed in activated spleen cells were significantly decreased by the dNP2-ctCTLA-4 fusion product. Specifically, the dNP2-ctCTLA-4 fusion product according to the present invention had at least 3 times lower expression level than the dNP2-EGFP fusion product.

TEST EXAMPLE 3

Analysis of Inhibitory Activity of ctCTLA-4 Peptide Variants Against IL-2 Expression in Spleen Cells 1) Evaluation of IL-2 Expression Inhibitory Ability of ctCTLA-4 Peptides and Variants Thereof IL-2 expression inhibitory abilities were compared between the ctCTLA-4 peptide purified in Production Example (represented by "WT" in the present Test Example) and 1YF (SEQ. ID. No. 5), 2YF (SEQ. ID. No. 6) or DYF (SEQ. ID. No. 7) variants purified in Production Example 2.

Figure 8:
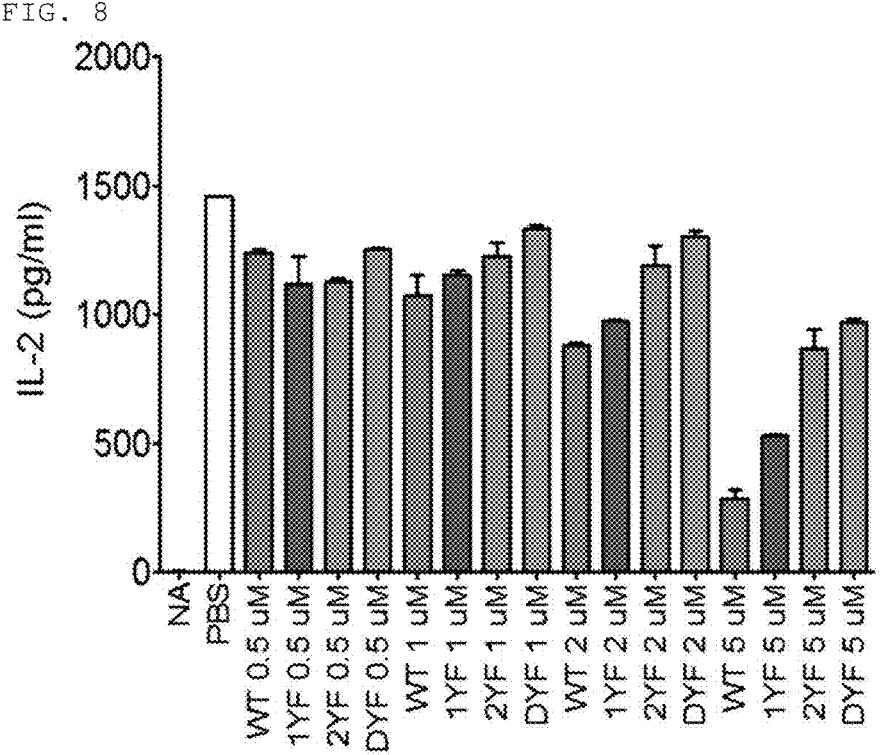
FIG. 8 is a graph showing measurement results of IL-2 expression inhibitory efficiencies of 0.5, 1, 2 or 5 μM WT, 1YF, 2YF and DYF. The numbers represent mean±standard deviation, * represents $p<0.05$, represents $p<0.01$, and * represents $p<0.001$; Student's t-test.

The spleen cells activated by the anti-CD3 and anti-CD28 antibodies were each treated with 0.5, 1, 2 or 5 μM WT, 1YF, 2YF and DYF, and IL-2 expression inhibitory abilities were measured by ELISA and are shown in FIG. 8.

At this time, the activated spleen cells were activated with anti-CD3/CD28 antibody in the presence of 1 μM PBS, 0.5, 1, 2 or 5 μM WT, 1YF, 2YF, DYF for 24 hours.

FIG. 8 is a graph showing measurement results of IL-2 expression inhibitory efficiencies of 0.5, 1, 2 or 5 μM WT, 1YF, 2YF and DYF. The numbers represent mean±standard deviation, * represents $p<0.05$, represents $p<0.01$, and * represents $p<0.001$; Student's t-test.

As can be seen from FIG. 8, 1YF, 2YF and DYF exhibited significant deterioration in IL-2 expression inhibitory efficiency, compared to WT. That is, it can be seen that the amino acid fragments of the ctCTTLA-4 peptide according to the present invention where 1Y and 2Y are located greatly contribute to inhibitory activity of IL-2 expression. The ctCTLA-4 fragment peptides (Sequence ID Nos. 2, 3 and 4) of areas including 1Y and 2Y amino acid residues also had excellent IL-2 expression inhibitory effects. The test showed fragment peptides which were the most active in ctCTLA-4.

TEST EXAMPLE 4

Analysis of Effects of Fusion Products in Spleen Cells

2) Analysis of Inhibitory Activity of dNP2-TAMRA, dNP2-ctCTLA-4 Fusion Product and dNP2-ctCTLA-4-fm3 Fusion Product Against Activation of CD4 T-Cells The present test was conducted to check whether or not the dNP2-TAMRA, dNP2-ctCTLA-4 fusion product and dNP2-ctCTLA-4-fm3 fusion product according to the present invention could inhibit activation of CD4 T-cells in the mouse model. At this time, CD25 was an activation marker which has an increasing expression level when T-cells were activated, and whether or not activation of CD4 T-cells was inhibited based on the amount of expressed CD25 was determined. Specifically, the test method was as follows.

A 96-well plate was coated with 0.1 μg of anti-CD3 and anti-CD28 antibodies in a cell incubator at 37° C. under 0.5% carbon dioxide for 5 hours. Then, isolated spleen cells of mice were seeded in a density of $2.5 \times 10^5$ on each well. The cells were treated with PBS or 0.1, 0.5, 1, 2 or 5 μM dNP2-TAMRA, dNP2-ctCTLA-4 or dNP2-ctCTLA-4-Fm, and then cultured in a cell incubator at 37° C. under 0.5% carbon dioxide for 24 hours. Then, the cells were stained with APC fluorescence-conjugated anti-CD4 mAb and PE fluorescence-fused anti-CD25 mAb at 4° C. for 20 minutes. Then, the cells produced through the aforementioned process were analyzed by a flow cytometer (FACS) to compare amounts of expressed CD25.

Figure 9:
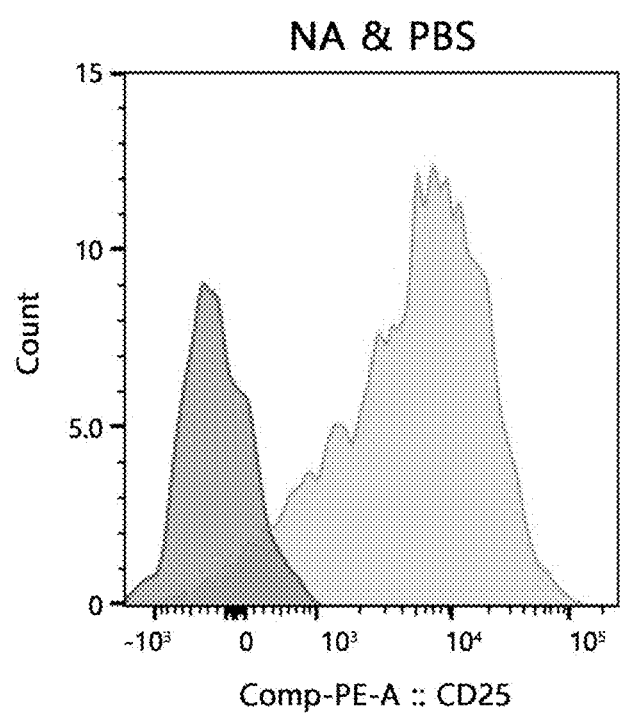
FIG. 9 is a graph showing introduction efficiency in primary mouse CD4-T cells treated with only PBS.
Figure 10:
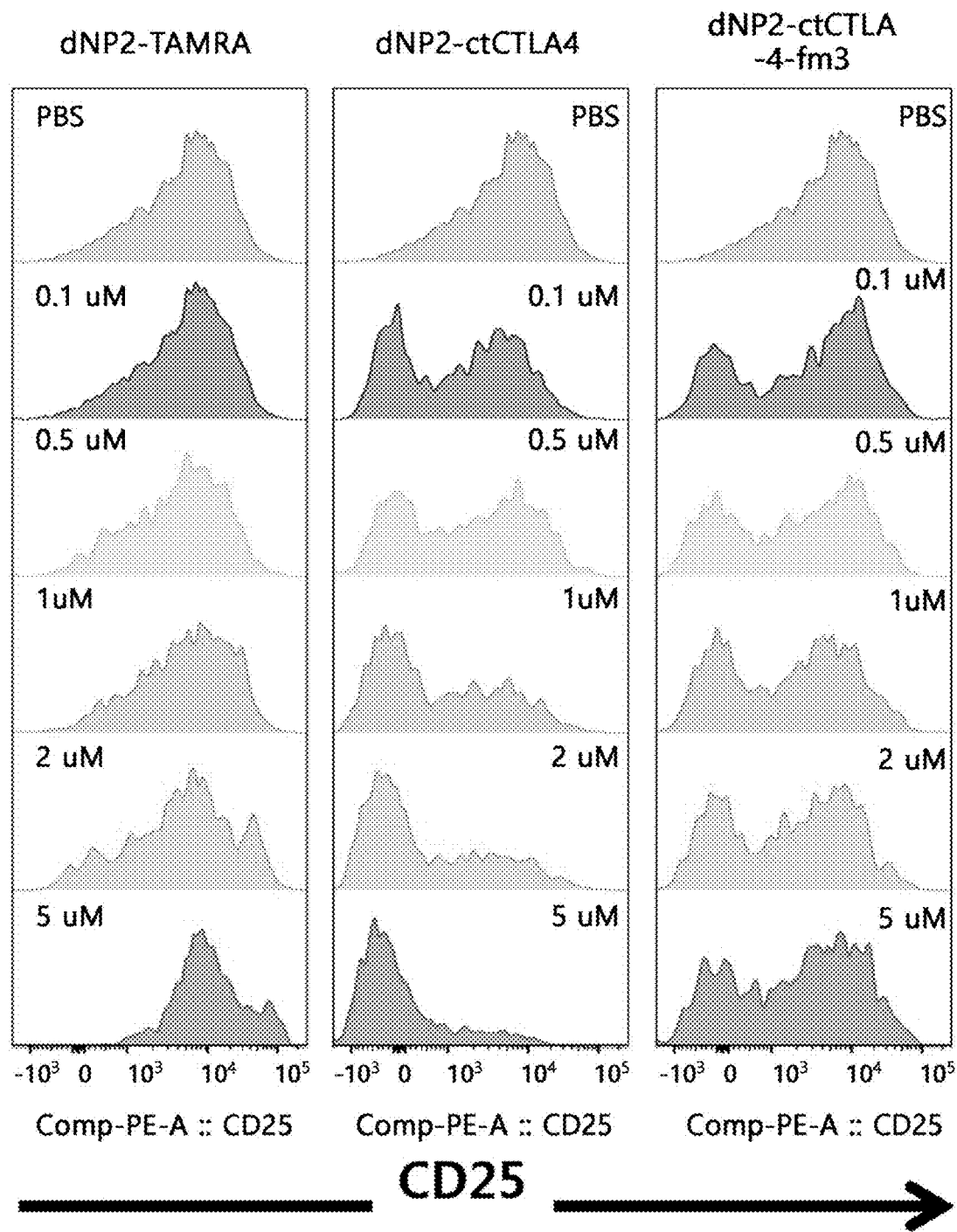
FIG. 10 is a graph showing intracellular transfer efficiencies of 0.1, 0.5, 1, 2 or 5 μM dNP2-TAMRA, dNP2-ctCTLA-4 fusion product and dNP2-ctCTLA-4-fm3 fusion product in primary mouse CD4-T-cells. "NA", as herein used, means a negative control group to which stimulus to activate T-cells is not applied and PBS herein used means a positive control group to which stimuli of anti-CD3 and anti-CD28 monoclonal antibodies are applied to activate T-cells.

FIG. 9 is a graph showing introduction efficiency of primary mouse CD4-T-cells (NA&PBS) treated with NA or PBS, and FIG. 10 is a graph showing intracellular transfer efficiencies of 0.1, 0.5, 1, 2 or 5 µM dNP2-TAMRA, dNP2-ctCTLA-4 fusion product and dNP2-ctCTLA-4-fm3 fusion product in primary mouse CD4-T-cells. "NA", as herein used, means a negative control group to which stimulus to activate T-cells was not applied and PBS herein used means a positive control group to which stimuli of anti-CD3 and anti-CD28 monoclonal antibodies were applied to activate T-cells.

In FIG. 9, NA is indicated by a red graph and PBS is indicated by a blue graph. In this case, regarding PBS treatment, CD3 is a T cell receptor and CD28 is a co-receptor, and monoclonal antibodies targeting the same were used to apply stimulus to the T cell receptor. That is, as shown in FIG. 16 the graph of PBS treated with the T cell receptor showed a great increase in CD25 expression, while the NA graph showed maintenance in CD25 expression because no stimulus was applied.

As can be seen from FIG. 10, CD25 expression was inhibited in proportion to the concentration of dNP2-ctCTLA-4 when dNP2-ctCTLA-4 was treated at different concentrations, and the dNP2-ctCTLA-4-fm3 also exhibited efficacy similar thereto. On the other hand, dNP2-TAMRA could not inhibit CD25 expression because it had no activity like ctCTLA-4. Furthermore, the dNP2-CTLA-4 fusion product could exhibit significant effects so long as it was used in a concentration of 2 µM or more, while the dNP2-ctCTLA-4-fm fusion product exhibited excellent intracellular transfer efficiency even at a concentration of 0.1 µM, like the dNP2-ctCTLA-4 fusion product.

Figure 11:
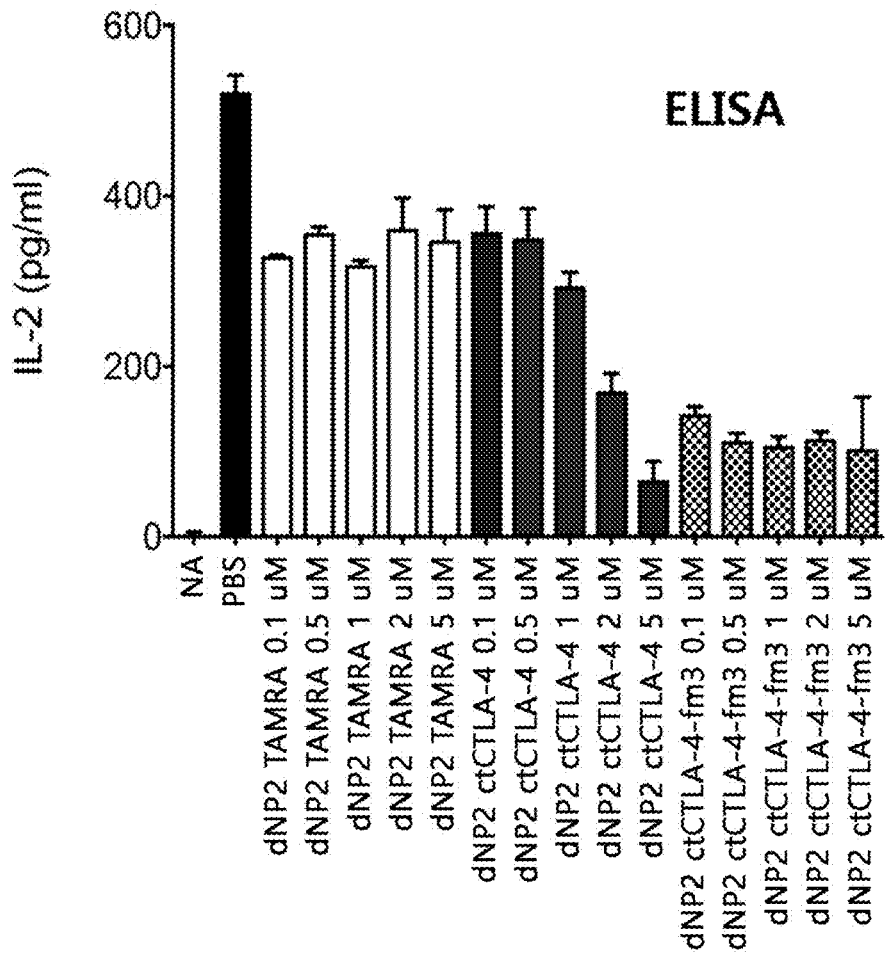
FIG. 11 is a graph showing IL-2 expression inhibitory efficiencies of 0.1, 0.5, 1, 2 or 5 μM dNP2-TAMRA fusion product, dNP2-CTLA-4 fusion product and dNP2-ctCTLA-4-fm3 fusion product. The numbers represent mean±s.d., * represents $p<0.05$, represents $p<0.01$, and *represents $p<0.001$; Student's t-test.

3) Evaluation of IL-2 Expression Inhibitory Abilities of Other Kinds of ctCTLA-4 Proteins The spleen cells activated by anti-CD3 and anti-CD28 antibodies were each treated with 0.1, 0.5, 1, 2 or 5 µM dNP2-TAMRA fusion product, dNP2-CTLA-4 fusion product and dNP2-ctCTLA-4-fm3 fusion product, and IL-2 expression inhibitory efficiency was measured by ELISA and is shown in FIG. 11. At this time, the activated spleen cells were activated with the anti-CD3/CD28 antibody in the presence of 1 µM PBS, 0.1, 0.5, 1, 2 or 5 µM dNP2-TAMRA fusion product, dNP2-CTLA-4 fusion product and dNP2-ctCTLA-4-fm3 fusion product for 24 hours.

FIG. 11 is a graph showing IL-2 expression inhibitory efficiencies of 0.1, 0.5, 1, 2 or 5 µM dNP2-TAMRA fusion product, dNP2-CTLA-4 fusion product and dNP2-ctCTLA-4-fm3 fusion product. The numbers represent mean±s.d., *represents $p<0.05$, represents $p<0.01$, and *represents $p<0.001$; Student's t-test.

The results shown in FIG. 11 indicated that the dNP2-TAMRA fusion product could never inhibit IL-2 expression. In addition, the dNP2-CTLA-4 fusion product also exhibited inhibitory effect on IL-2 expression, but the effect was significant only at 2 µM or more.

Finally, the dNP2-ctCTLA-4-fm fusion product, which was obtained using fragments of ctCTLA-4 according to the present invention, exhibited excellent inhibitory activity against IL-2 expression, comparable to the dNP2-ctCTLA-4 fusion protein.

TEST EXAMPLE 5

Inhibitory Activities of Fusion Product Against T Cell Activation and Chemokine Receptor Expression in PBMC Cells The previous tests showed effects of CTLA-4(dNP2-ctCTLA-4) in spleen cells. Accordingly, in the present Test Example, in vitro analysis targeting PBMCs was conducted in order to identify the function of dNP2-ctCTLA-4 to inhibit human T cells. PBMCs were stimulated with anti-CD3 and anti-CD28 monoclonal antibodies, treated with PBS, dNP2-EGFP and dNP2-ctCTLA-4, and cultured for 12 hours, and then activation marker and cytokine production degrees were analyzed (Test method 19).

Figure 12A:
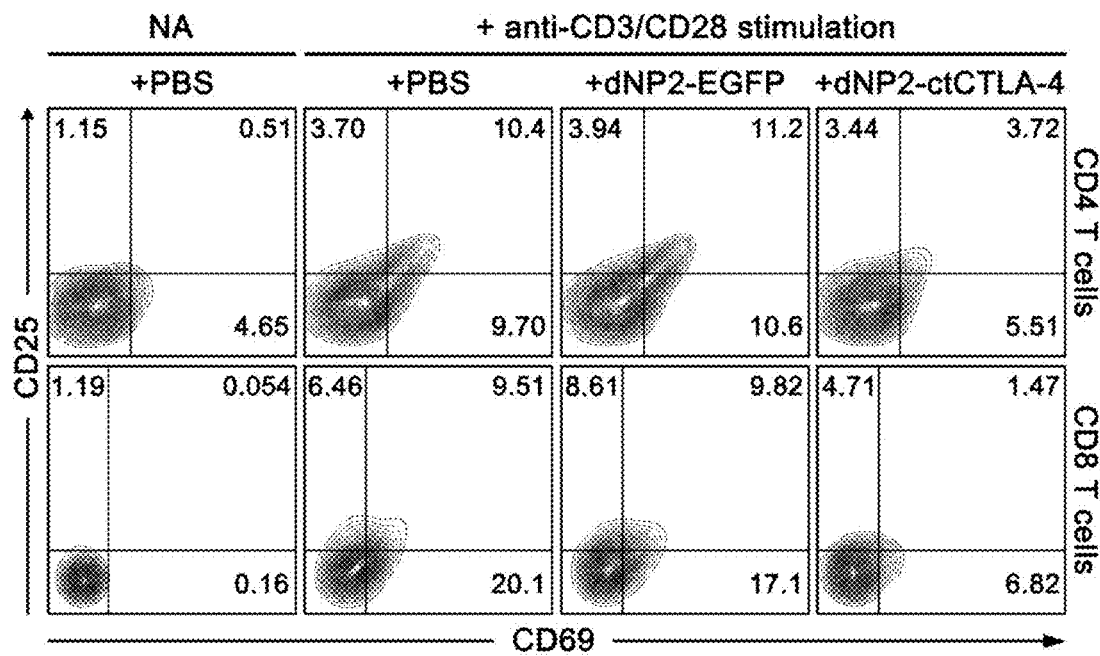
FIGS. 12A to 12C show that PBMC cells are stimulated with anti-CD3 and anti-CD28 monoclonal antibodies for 12 hours. Specifically.
Figure 12B:
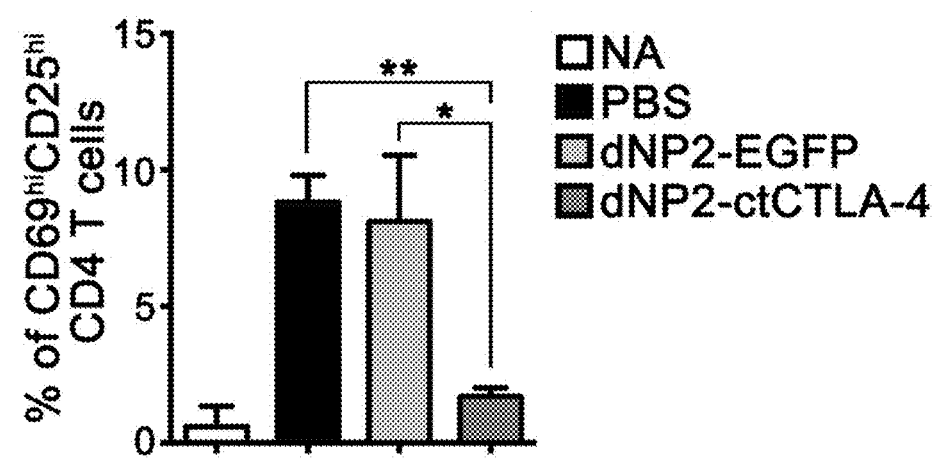
Figure 12C:
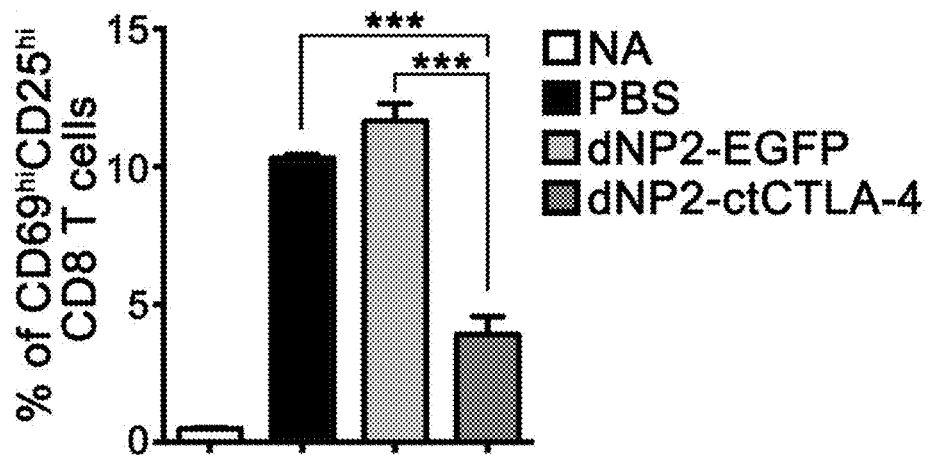

FIGS. 12A to 12C show that PBMC cells are stimulated with anti-CD3 and anti-CD28 monoclonal antibodies for 12 hours. Specifically, FIGS. 12A and 12B are graphs showing results of flow cytometry after staining with anti-CD4, anti-CD8, anti-CD69 and anti-CD25 fluorescent-labeled antibodies, and FIG. 12C is a graph showing analysis of IL-2 concentrations of the culture supernatant using an IL-2 ELISA kit.

Figure 12D:
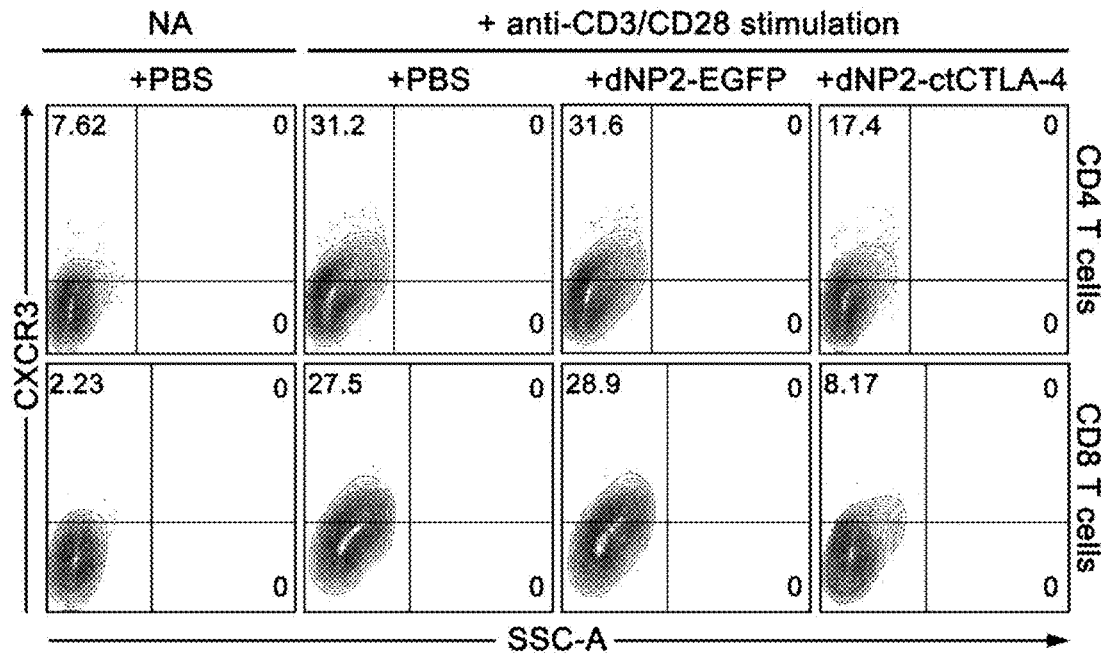
FIGS. 12D to 12F show that PBMC cells are stimulated with anti-CD3 and anti-CD28 monoclonal antibodies for 48 hours, and more specifically, are graphs showing results of flow cytometry after staining with anti-CD4, anti-CD8 and anti-CXCR3 fluorescent labeled antibodies.
Figure 12E:
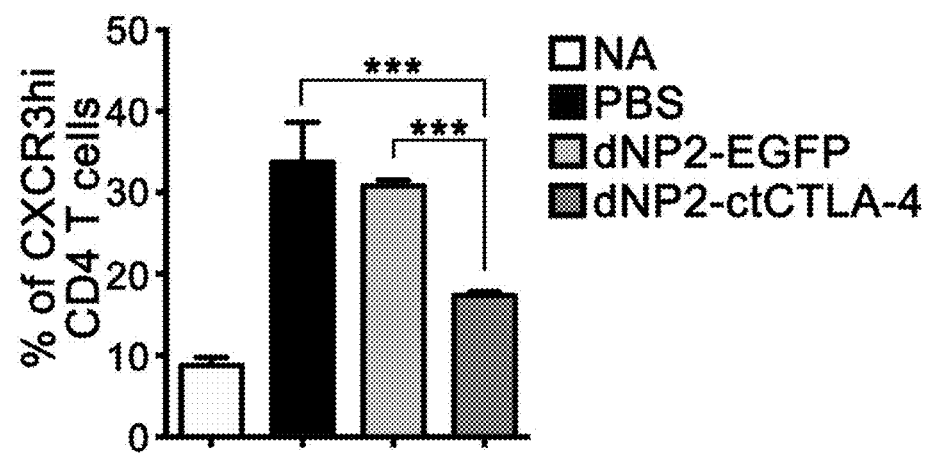
Figure 12F:
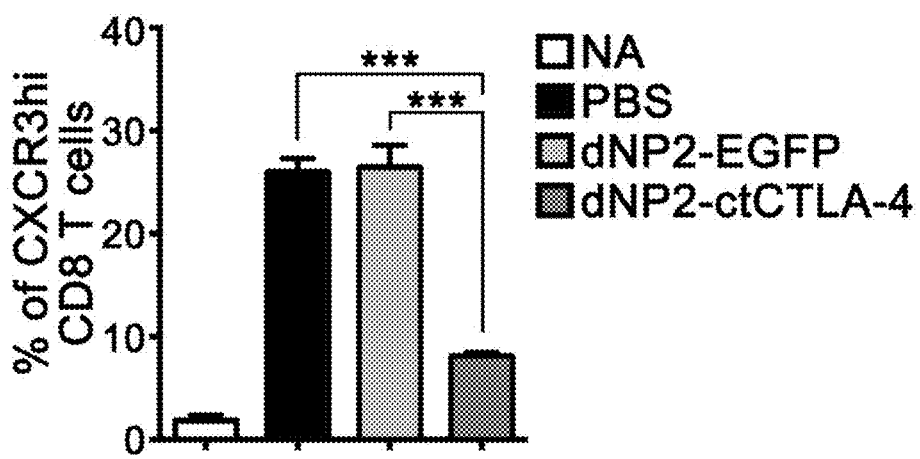

FIGS. 12D to 12F show that PBMC cells are stimulated with anti-CD3 and anti-CD28 monoclonal antibodies for 48 hours, and more specifically, are graphs showing results of flow cytometry after staining with anti-CD4, anti-CD8 and anti-CXCR3 fluorescent labeled antibodies. For each group, n is 3, and the bar graph is represented by mean±standard deviation. ***represents $p<0.001$.

As shown in FIG. 12, dNP2-ctCTLA-4 inhibited expression of early activation markers of human T cells. Specifically, FIGS. 12A and 12B showed that both CD4 and CD8 T cells treated with dNP2-ctCTLA-4 had significant low expression of CD69 and CD25. As can be seen from FIG. 12C, when treating with dNP2-ctCTLA-4, IL-2 production was more significantly reduced, than when treating with PBS or dNP2-EGF, which indicates that dNP2-ctCTLA-4 effectively inhibited T cell activation.

CXCR3 is a chemokine receptor on T cell surfaces rapidly induced by TcR stimuli, which causes permeation of cells into inflammation sites. As can be seen from FIGS. 12D and 12F, surface expression levels of CXCR3 were significantly increased in CD4 and CD8 T cells activated through treatment with anti-CD3 and CD28 antibodies for 48 hours. On the other hand, expression of CXCR3 was significantly reduced in cells treated with dNP2-ctCTLA-4. That is, T cells having dNP2-ctCTLA-4 cannot function as effectors and do not have the migration ability to invade tissues.

TEST EXAMPLE 6

Figure 13A:
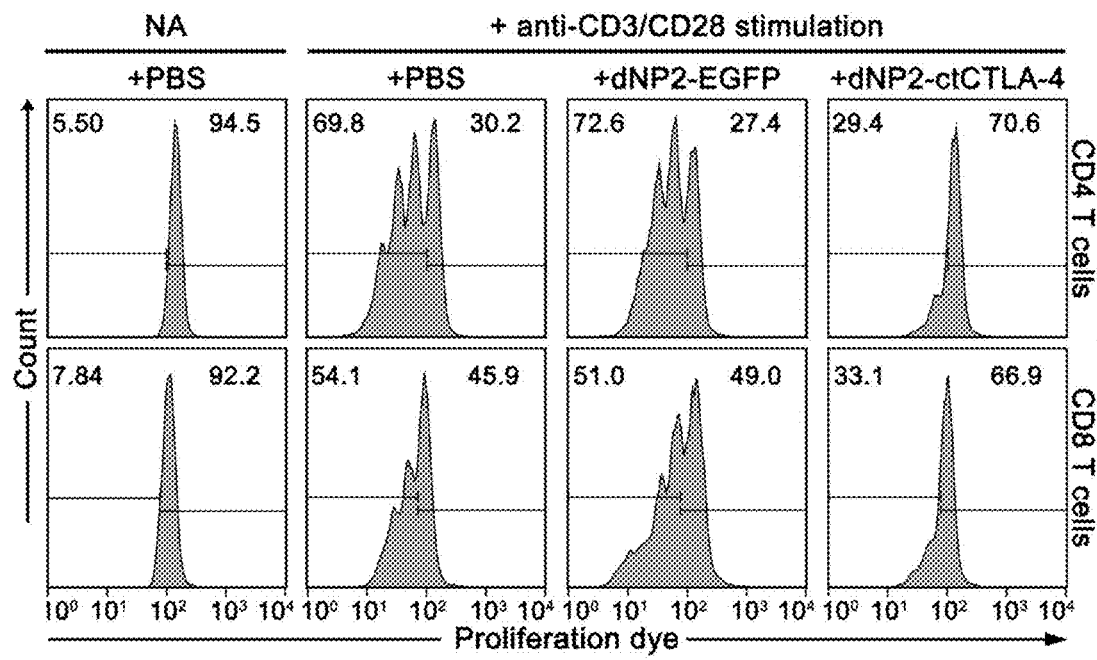
FIGS. 13A to 13C are graphs showing results of flow cytometry of human CD4 T cells and CD8 T cells, after separating human CD4 T cells and CD8 T cells from PBMC by magnetic-activated cell sorting (MACS), staining with eFluor 670 (cell proliferation dye) and stimulating with anti-CD3 and anti-CD28 monoclonal antibodies for 5 days. At this time, the anti-CD4 fluorescent labeled antibodies was used for staining.
Figure 13B:
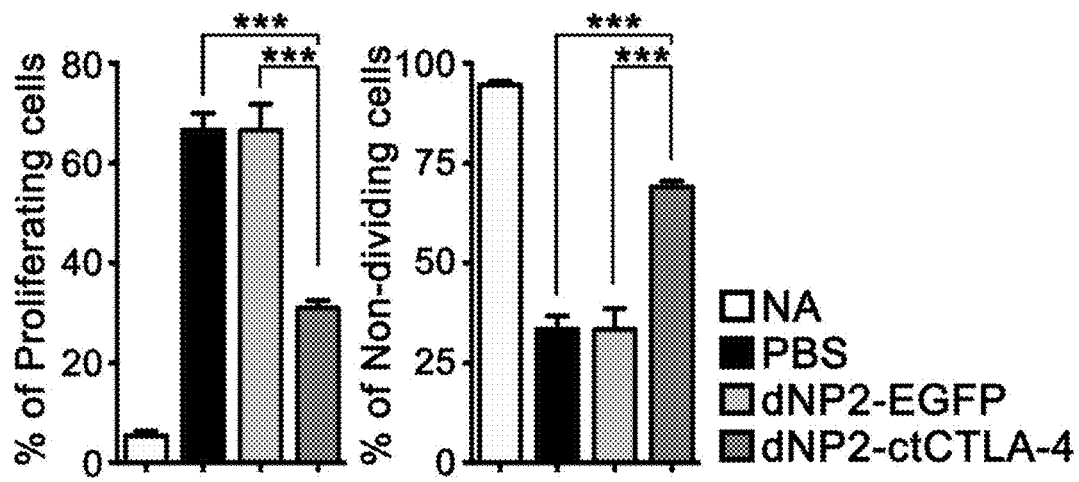
Figure 13C:
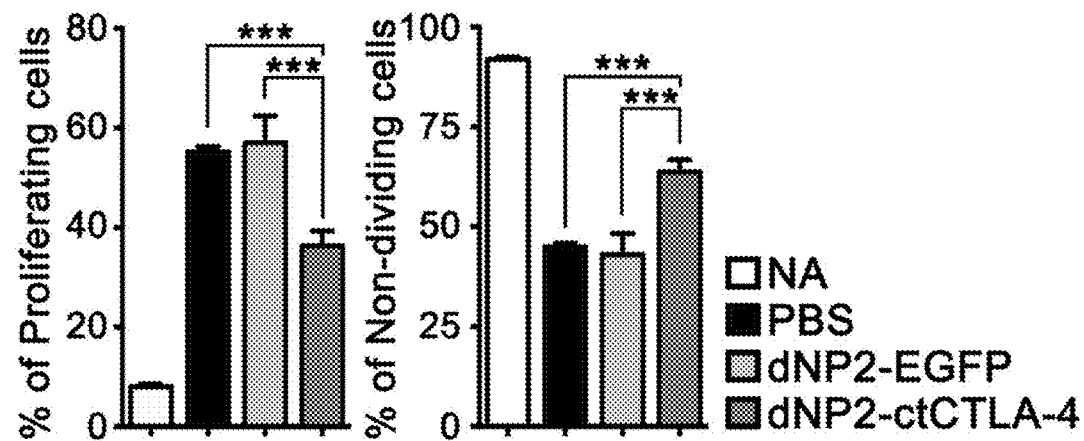

Analysis of Inhibitory Activity Against Proliferation and Production of Effector Molecules in Human T Cells FIGS. 13A to 13C are graphs showing results of flow cytometry of human CD4 T cells and CD8 T cells, when separating human CD4 T cells and CD8 T cells from PBMC by magnetic-activated cell sorting (MACS), staining with eFluor 670 (cell proliferation dye) and stimulating with anti-CD3 and anti-CD28 monoclonal antibodies for 5 days. At this time, the anti-CD4 fluorescent labeled antibodies was used for staining.

Figure 13D:
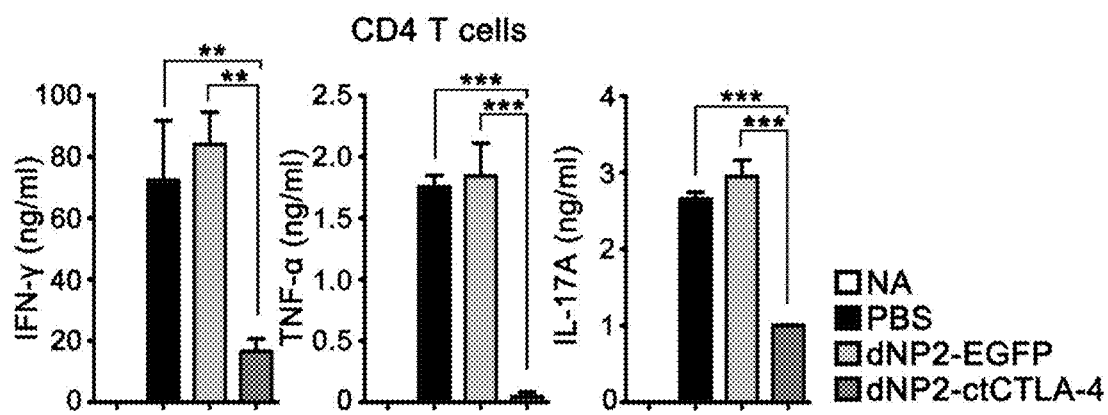
FIG. 13D is a graph showing results of analysis of the culture supernatant of CD4 T cells isolated with IFN-γ, TNF-a and IL-17A ELISA kit.
Figure 13E:
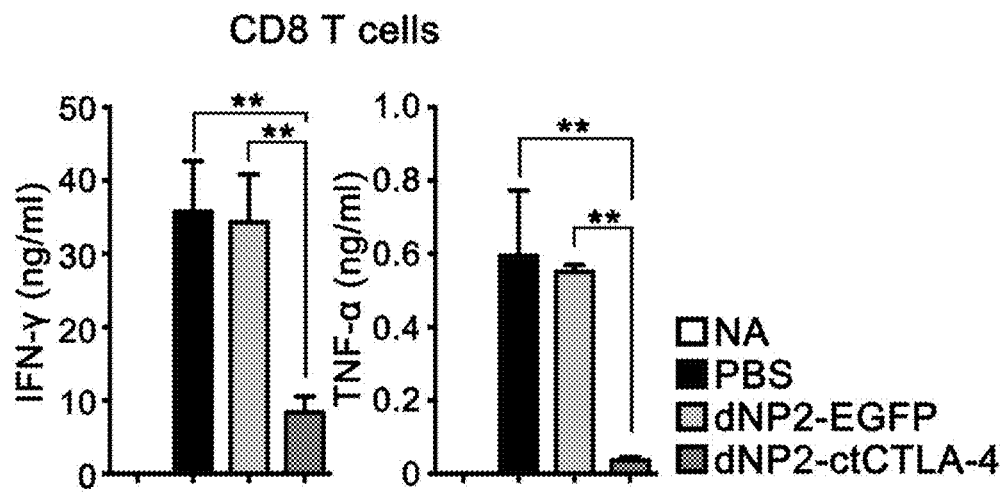
FIG. 13E is a graph showing results of analysis of the culture supernatant of CD8 T cells isolated with IFN-γ and TNF-a ELISA kit.

FIG. 13D is a graph showing analysis of the culture supernatant of CD4 T cells isolated with IFN-γ, TNF-a and IL-17A ELISA kit, and FIG. 13E is a graph showing analysis of the culture supernatant of CD8 T cells isolated with IFN-γ and TNF-a ELISA kit.

Figure 13F:
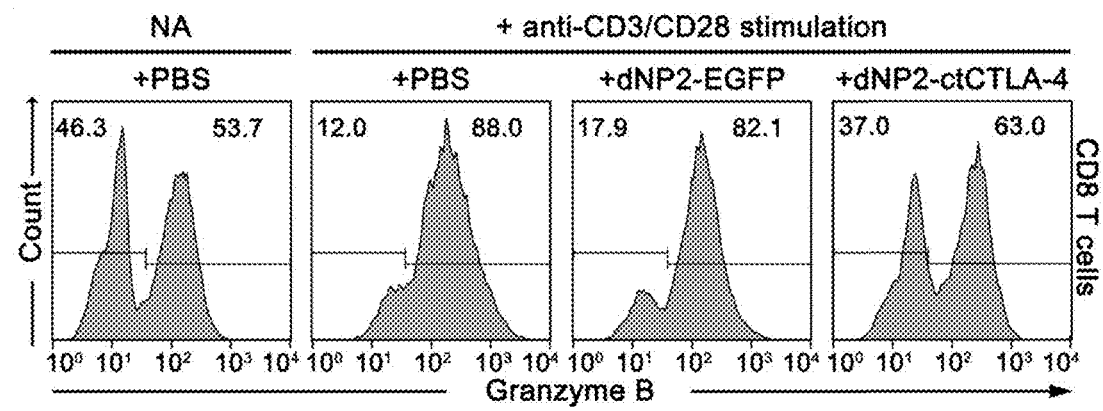
FIGS. 13F and 13G are graphs showing results of flow cytometry after staining with anti-CD8 and anti-Granzyme B fluorescent labeled antibodies. The graph shows results obtained from tests conducted repeatedly three times and the bar graph is represented by mean±standard deviation. Student's t-test was used for statistics, represents $p<0.01$, and *represents $p<0.001$.
Figure 13G:
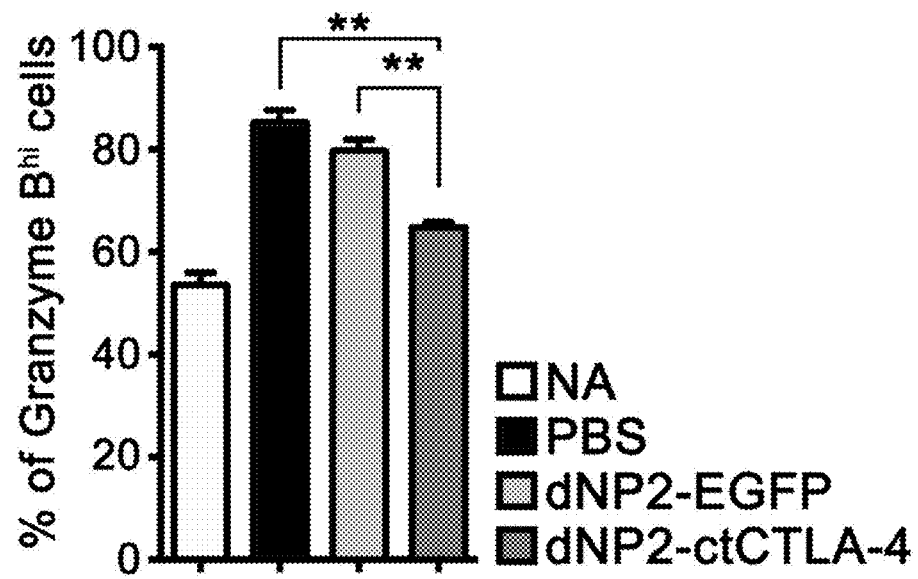

In addition, FIGS. 13F and 13G are graphs showing flow cytometry after staining with anti-CD8 and anti-Granzyme B fluorescent labeled antibodies. The graph shows results obtained from tests conducted repeatedly three times and the bar graph is represented by mean±standard deviation. Student's t-test was used for statistics, represents p<0.01, and *represents p<0.001.

In order to analyze variations in human T cells induced by dNP2-ctCTLA-4 more accurately, in the present Test Example, effects of in vitro activated human CD4 and CD8 T cells on proliferation and effector molecules were analyzed. In the present test, human CD4 and CD8 T cells obtained from PBMC cells by magnetic-activated cell sorting (MACS) were used. The cells were strained with a cell proliferation dye (efluor 670) and stimulated in the presence of 1 μM dNP2-ctCTLA-4 with anti-CD3 and CD28 antibodies for 5 days.

As shown in FIGS. 13A to 13C, analysis results of the number of cell divisions based on the peak division showed that dNP2-ctCTLA-4 significantly reduced proliferation of CD4 and CD8 T cells. In addition, as can be seen from FIGS. 13D and 13E, inflammatory cytokine including IFN-γ, TNF-a and IL-17A was significantly reduced by dNP2-ctCTLA-4, as compared to the PBS or dNP2-EGFP treatment group.

Since cytotoxicity mediating CD8 T cells plays a key role in allograft rejection, whether or not dNP2-ctCTLA-4 has inhibitory activity against expression of Granzyme B in CD8 T cells was analyzed. As shown in FIGS. 13F and 13G, about half all separated CD8 T cells were Granzyme $B^{hi}$ ($GzmB^{hi}$) cells and most thereof were anti-CD3 and CD28 antibodies which induced production of GzmB after stimulating for 5 days. Treatment with dNP2-ctCTLA-4 significantly reduced GzmB expression, as compared to the control group, which was almost the same pattern as non-activated conditions.

The aforementioned results showed that dNP2-ctCTLA-4 potently inhibited proliferation of human CD4 and CD8 T cells, production of effector molecules and cytokine, and proliferation and production of effector molecules by human T cells, thereby preventing allograft rejection.

TEST EXAMPLE 7

Preventive or Therapeutic Effects of Human Skin Allograft Rejection in Animal Models In order to identify whether or not in vivo response of human T cells can be controlled by dNP2-ctCTLA-4, in the present Test Example, SCID/beige mice, human skin graft models were used.

Split thickness human skin grafts, dermatomed from discarded tissues of unidentified donors that contain the papillary dermis and its superficial vascular plexus in addition to the epidermis, were transplanted onto the dorsa of a cohort of adult mice at 12-16 weeks of age. After 4-5 weeks, when the grafts were completely healed, as determined by visual inspection, $2\times10^8$ human peripheral blood mononuclear cells (PBMCs) from another donor allogeneic to the skin donor were injected intraperitoneally into the animals. In this model, circulating effector memory T cells that directly recognize non-self class I and class II MHC molecules expressed on graft cells are recruited to the graft and mediate human microvessel destruction. For the next 2 weeks, we intraperitoneally injected 50 μg of dNP2-ctCTLA-4 or phosphate-buffered saline (PBS) into half of the mouse cohort every other day (FIG. 14A).

Figure 14A:
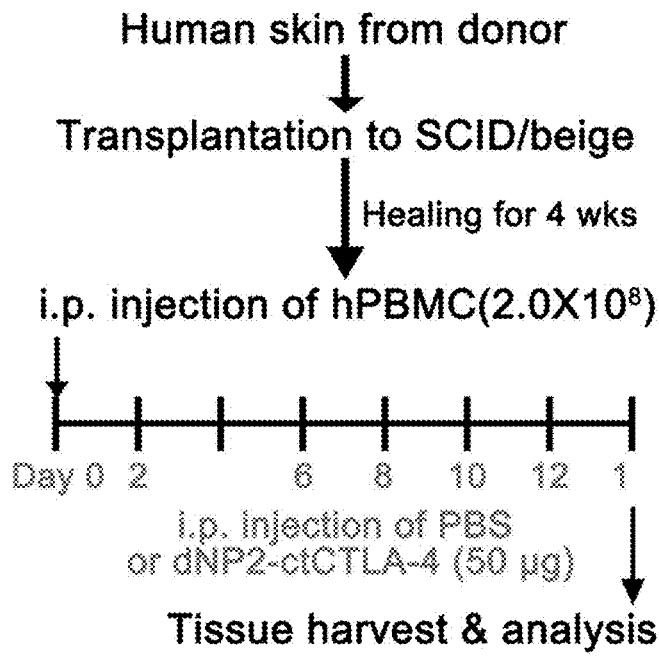
FIG. 14A is a graph showing a test design of human skin allograft rejection model.
Figure 14B:
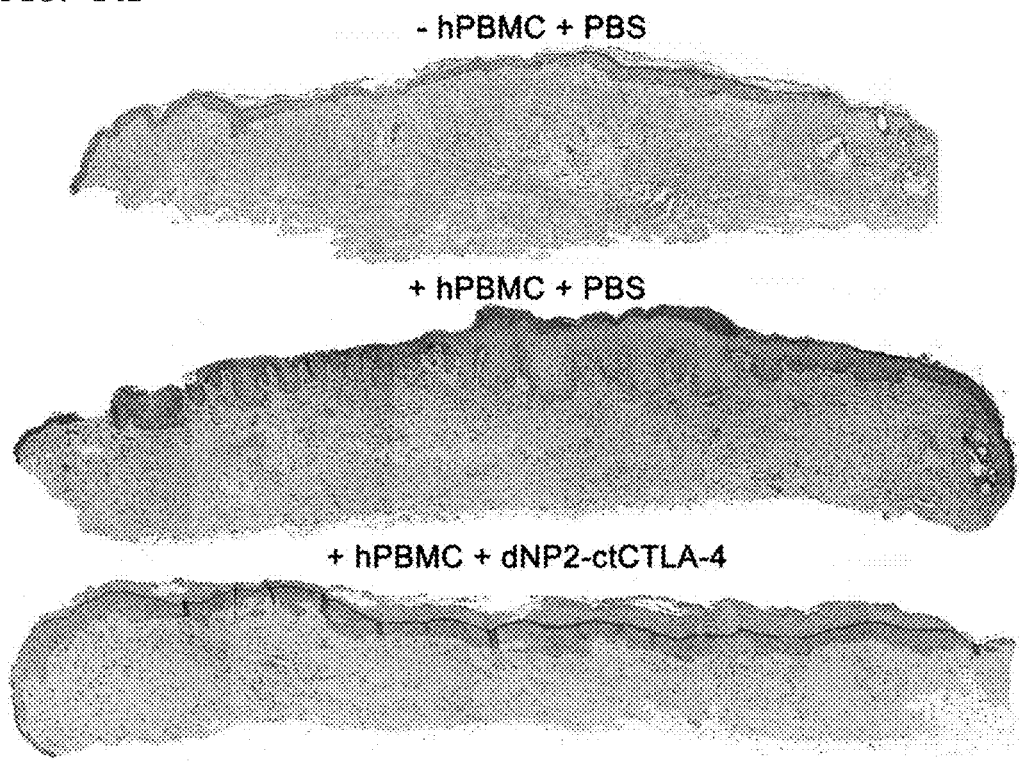
FIG. 14B is an image obtained after harvesting skin grafts on the $14^{th}$ day, producing paraffin blocks, cutting the same and staining with hematoxylin and eosin (H & E), and imaging the entire fragment tissue by bright-field microscopy.
Figure 14C:
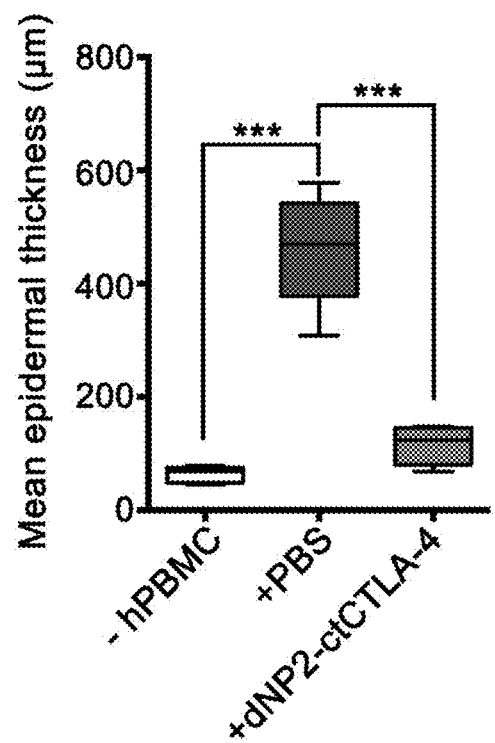
FIG. 14C is a graph showing the mean epidermal thickness in the entire fragment tissue measured in FIG. 14B using ImageJ 1.50i software.
Figure 14D:
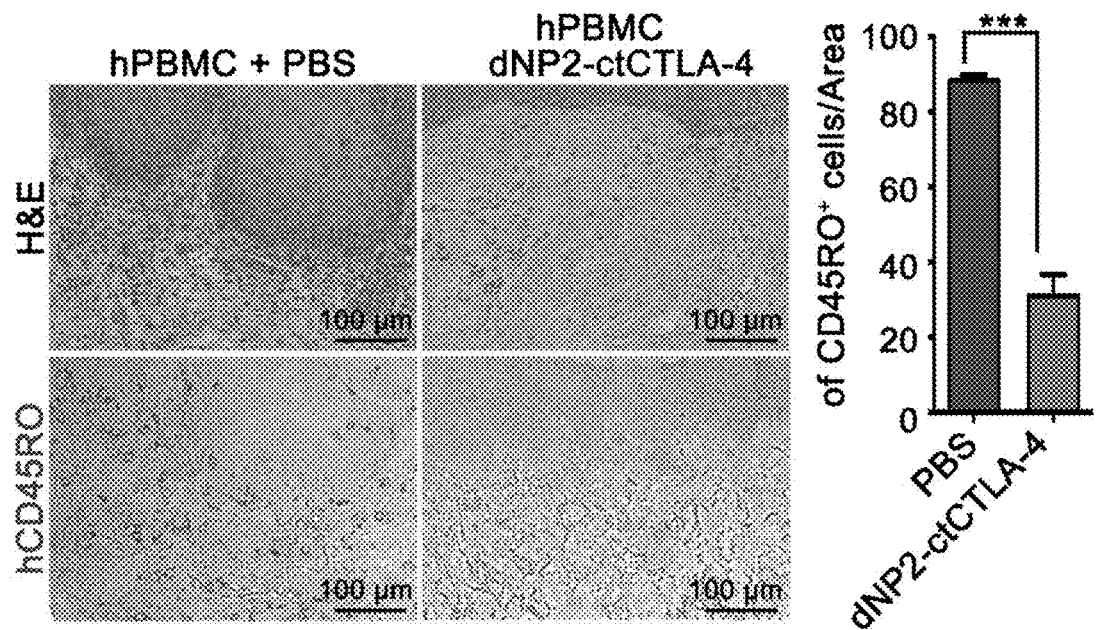
FIG. 14D is a graph showing results of detection using 3,3'-diaminobenzide (DAB) substrate after staining paraffin fragment tissue with anti-human CD45RO antibodies and applying horseradish peroxidase (HRP)-conjugated secondary antibody thereto.

FIG. 14A is a graph showing a test design of human skin allograft rejection model, and FIG. 14B is an image obtained after harvesting skin grafts on the $14^{th}$ day, producing paraffin blocks, cutting the same and staining with hematoxylin and eosin (H & E), and imaging the entire fragment tissue by bright-field microscopy. FIG. 14C is a graph showing the mean epidermal thickness in the entire fragment tissue measured in FIG. 14B using ImageJ 1.50i software. FIG. 14D is a graph showing results of detection using 3,3'-diaminobenzide (DAB) substrate after staining paraffin fragment tissue with anti-human CD45RO antibodies and applying horseradish peroxidase (HRP)-conjugated secondary antibody thereto. Hematoxylin was used for counter staining. CD45RO+ cells were counted using ImageJ 1.50i software.

Figure 14E:
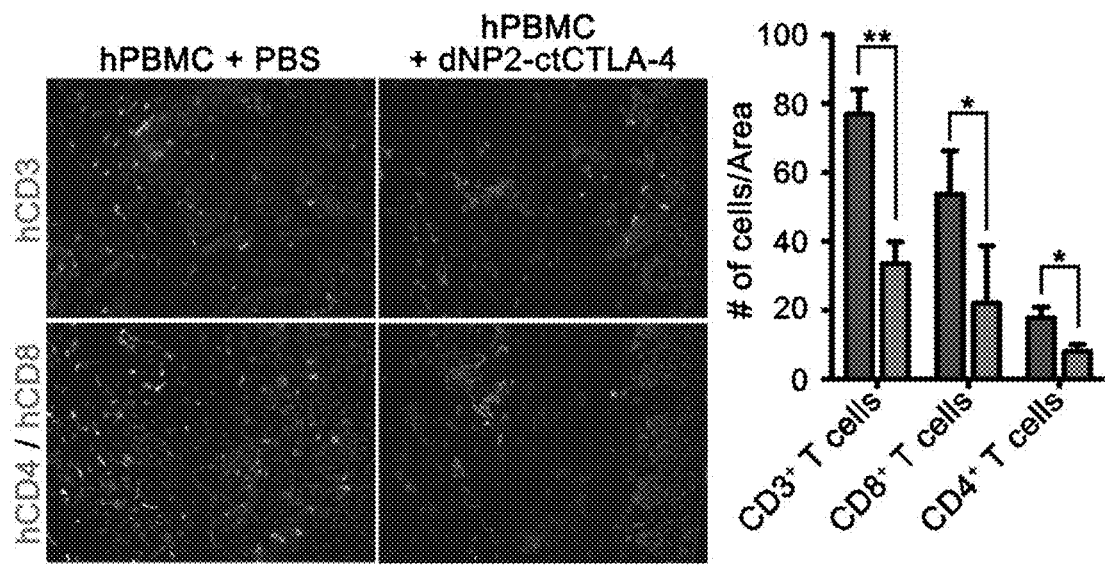
FIG. 14E shows that another part of the harvested skin grafts was prepared as frozen blocks and stained with anti-human CD3-PE or anti-human CD4-FITC and anti-human CD8-FITC antibodies. DAPI was used for nuclear staining.

Referring to FIG. 14E, another part of the harvested skin grafts was prepared as frozen blocks and stained with anti-human CD3-PE or anti-human CD4-FITC and anti-human CD8-FITC antibodies. DAPI was used for nuclear staining. The slides were observed by fluorescence microscopy. Marker-positive cells were counted using ImageJ 1.50i software.

FIG. 14 shows results obtained from tests conducted repeatedly three times and the bar graph is represented by mean±standard deviation. Student's t-test was used and * indicates p<0.05, indicates p<0.01, and *indicates p<0.001.

As shown in FIGS. 14B and 14C, upon harvest at 14 days, grafts analyzed by histology from mice that had received PBMCs and PBS showed thickening of the epidermis with elongated rete ridges, dermal and epidermal lymphocytic infiltration, and nuclei within the stratum corneum, while grafts from mice that had not received PBMCs showed no signs of inflammation. In contrast, grafts from dNP2-ctCTLA-4-treated mice showed dramatically reduced epidermal thickness and cell infiltration. By immunohistochemistry, significant human CD45RO+ lymphocyte infiltration was observed in PBS control skin grafts, while few skin-infiltrated lymphocytes were detected in the dNP2-ctCTLA-4-treated group (FIG. 14d). Infiltrated cells were mainly CD3+ T cells with a higher frequency of CD8+ T cells (red) than CD4+ T cells (green) in grafts from the control group (FIG. 14e). In other words, dNP2-ctCTLA-4 treatment significantly reduced T cell infiltration. Importantly, circulating levels of human PBMCs in the blood were not significantly changed in the dNP2-ctCTLA-4-treated group compared to the control group. These results suggest that dNP2-ctCTLA-4 can reduce human T cell infiltration into grafted skin tissues and significantly ameliorate graft inflammation.

TEST EXAMPLE 8

Figure 15A:
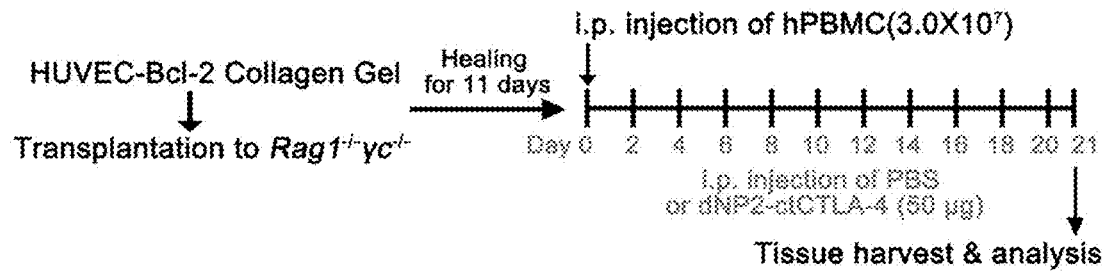
FIG. 15A is a graph showing a test design of an HUVEC-collagen tissue allograft model.
Figure 15B:
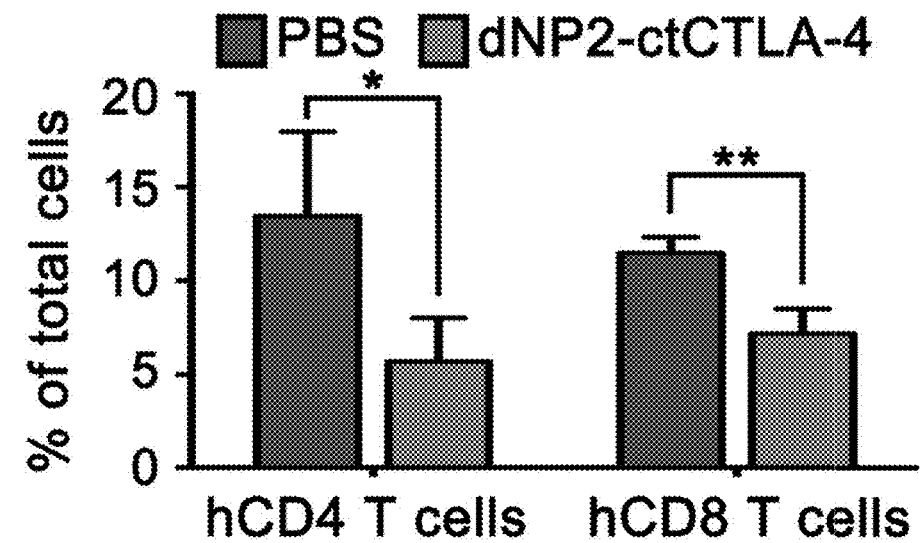
FIG. 15B is a graph showing results of flow cytometry after obtaining the blood of mice on the $21^{st}$ day by cardiac puncture and staining with anti-human CD4 and CD8 fluorescent labeled antibodies.
Figure 15C:
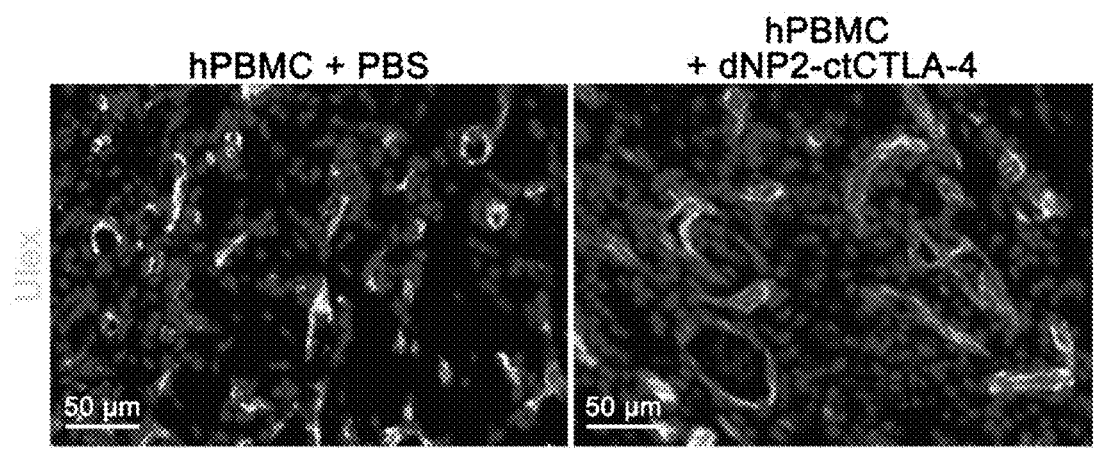
FIG. 15C shows counting results of CD45RO$^+$ cells using ImageJ 1.50i software after harvesting collagen gel from the mice, preparing the blocks into paraffin blocks, staining the blocks with anti-human CD45RO antibody and counter staining the blocks with hematoxylin.
Figure 15D:
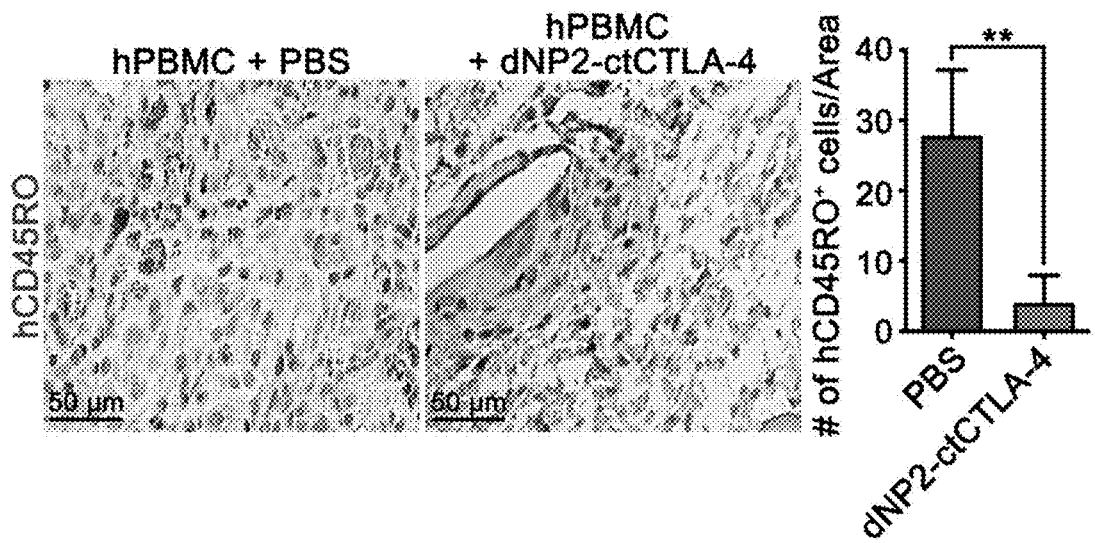
FIG. 15D shows results of fluorescence microscopy after staining the paraffin blocks using fluorescein-labelled Ulex Europaeus Agglutinin I (UEA I)
Figure 15E:
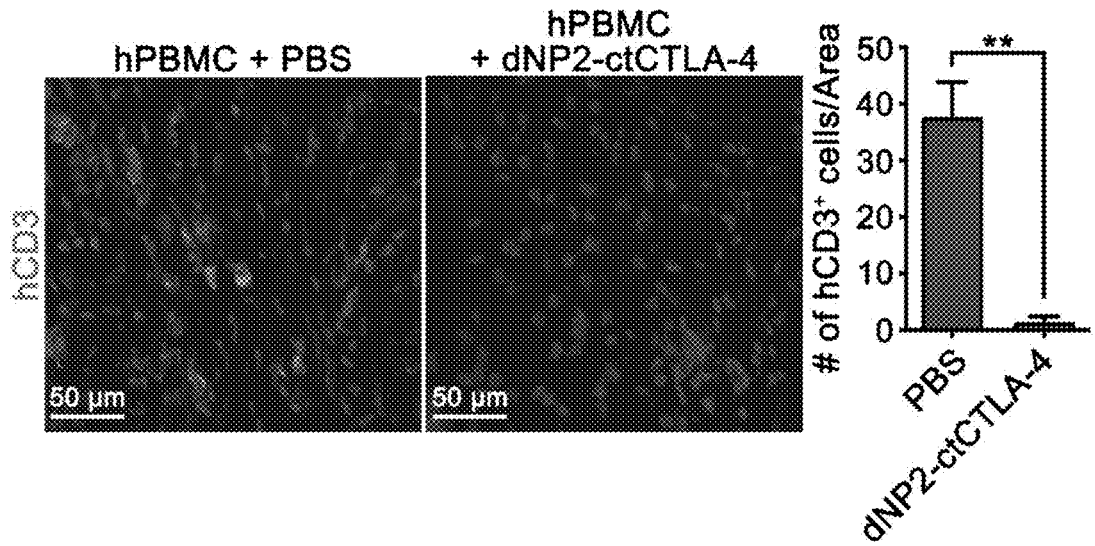
FIG. 15E shows counting results of CD3+ cells with ImageJ 1.50i software, after preparing another part of the tissues as frozen blocks, staining with anti-human CD3-PE antibody, and staining the nucleus with DAPI.
Figure 15F:
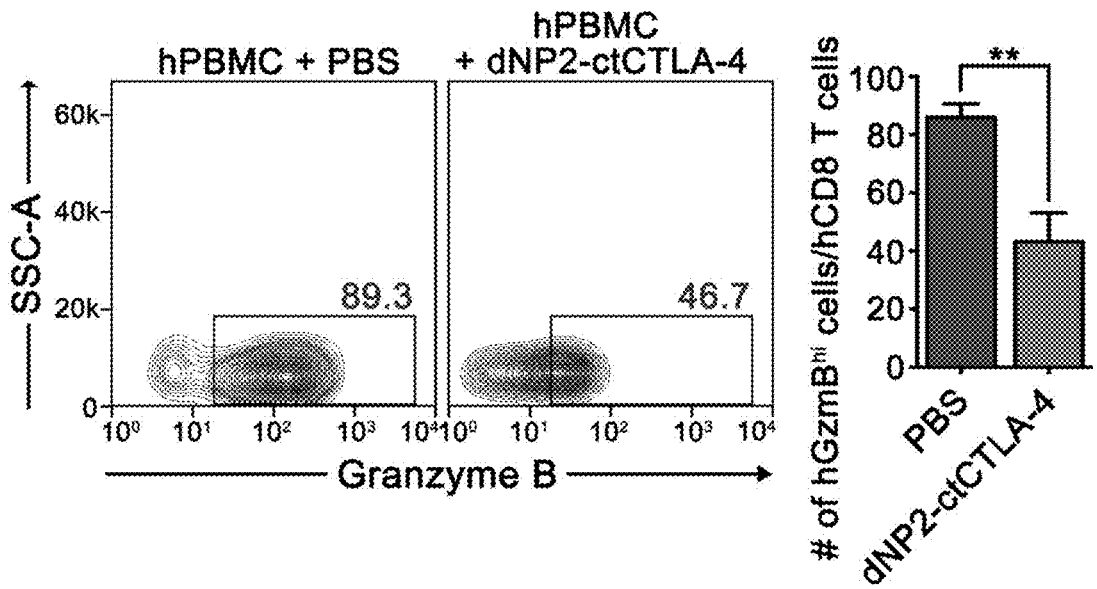
FIG. 15F shows analysis results of lymphocytes in the blood by flow cytometry after staining with anti-human CD8 and granzyme B or anti-human CD4 and Foxp3 fluorescently-labelled antibodies.

Inhibitory Activity of T Cell-Mediated Graft Rejection in HUVEC-Collagen Gel-Grafted Humanized Mice FIG. 15A is a graph showing a test design of an HUVEC-collagen tissue allograft model. FIG. 15B is a graph showing flow cytometry after obtaining the blood of mice on the $21^{st}$ day by cardiac puncture and staining with anti-human CD4 and CD8 fluorescent labeled antibodies. As shown in FIG. 15C, collagen gel from the mice was harvested and prepared into paraffin blocks. The blocks were stained with anti-human CD45RO antibody and counter stained with hematoxylin. CD45RO⁺ cells were counted using ImageJ 1.50i software. Referring to FIG. 15D, the paraffin blocks were stained using fluorescein-labelled Ulex Europaeus Agglutinin I (UEA I) and observed by fluorescence microscopy. Referring to FIG. 15E, another part of the tissues was prepared as frozen blocks and stained with anti-human CD3-PE antibody, and the nucleus was stained with DAPI. CD3⁺ cells were counted with ImageJ 1.50i software. Referring to FIGS. 15F and 15G, the lymphocytes in the blood were analyzed by flow cytometry after staining with anti-human CD8 and granzyme B or anti-human CD4 and Foxp3 fluorescently-labelled antibodies.

FIG. 15 shows results obtained from respective tests conducted repeatedly 9 times (PBS) and 8 times (dNP2-ctCTLA-4) and the bar graph is represented by mean±standard deviation. Student's t-test was used and * indicates $p<0.05$, and ** indicates $p<0.01$.

As shown in FIG. 15, dNP2-ctCTLA-4 inhibited human mouse T cell-mediated immune reaction in HUVEC-collagen gel graft. Specifically, the human skin graft model involves potential roles for both antigen presentation and immune modulation by many different cell types, including resident leukocytes that could be affected by dNP2-ctCTLA-4. To more precisely delineate the effect on T cells, we employed a different graft model involving synthetic human microvessels formed by suspending Bcl-2 transduced HUVECs in a protein gel formed using rat tail type I collagen and human plasma fibronectin and then implanting such gels into the abdominal walls of immunodeficient mice. A previous study showed that Bcl-2-HUVEC-lined microvessels, which form spontaneously, anastomose with mouse microvessels so that they are perfused. At this time point, adoptively transferred alloreactive T cells, primed against HUVECs from the same donor, will expand in the circulation and infiltrate these synthetic tissues whereas T cells primed against a different HUVEC donor do not. Unlike microvessels formed from untransduced HUVECs, the infiltrating T cells do not destroy synthetic microvessels formed from Bcl-2-transduced cells, allowing T cell infiltrates to accumulate. We used this reductionist system to confirm that the effects of dNP2-ctCTLA-4 were being exerted on T cells. Specifically, we assembled HUVEC-collagen gel in vitro using Bcl-2-transfected cells and implanted the gels subcutaneously into RAG1 and IL2RG double knockout (DKO) mice. After 11 days, human PBMCs were injected into mice and treated with dNP2-ctCTLA-4 or PBS intraperitoneally for 3 weeks every other day (FIG. 15a). In blood circulating cells, the proportion of CD4 and CD8 T cells was significantly reduced by dNP2-ctCTLA-4 treatment (FIG. 15b), suggesting either inhibition of homeostatic proliferation, which was not seen in the skin graft experiments, or inhibition of antigen-specific expansion of T cells. In the HUVEC-collagen gel tissues, we observed similar levels of live endothelial cells in both groups by Ulex staining (FIG. 15c). However, CD45RO⁺ or CD3⁺ human T cell infiltration in the gel tissue was significantly reduced by dNP2-ctCTLA-4 treatment (FIGS. 15d and e). In addition, circulating CD8 T cells in the peripheral blood of dNP2-ctCTLA-4-treated mice showed a significantly lower frequency of granzyme B expression than the control group (FIG. 15f), indicating that dNP2-ctCTLA-4 inhibits both human CD4 and CD8 T cell activation and recruitment. Interestingly, we found that dNP2-ctCTLA-4 treatment significantly increased Foxp3⁺ regulatory CD4 T cells in the peripheral blood, which may down-regulate T cell-mediated alloresponses, consistent with the positive signaling role that CTLA-4 plays in this cell type.

TEST EXAMPLE 9

Figure 16A:
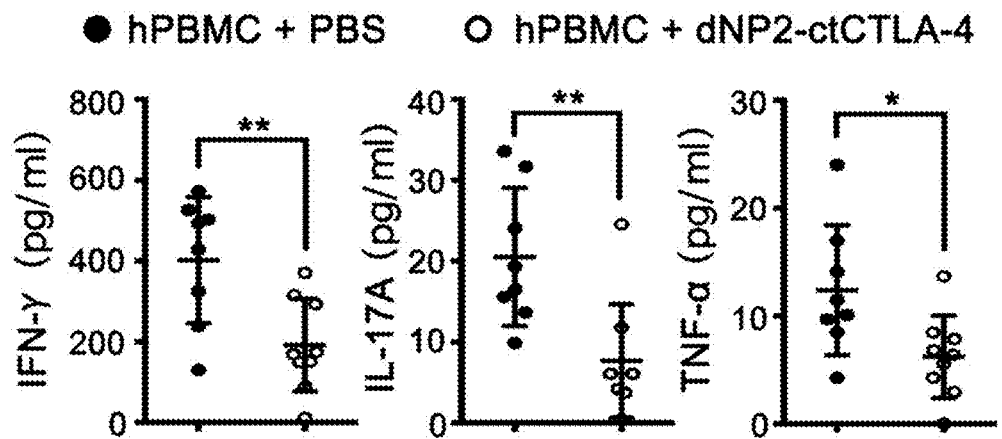
FIGS. 16A and 16B are graphs showing multi-plex Luminex assay on serum from HUVEC-collagen tissue allografted mice to analyze serum concentrations of IFN-γ, IL-17A, TNFa, CCL2, CCL3, CCL4, CXCL9, CXCL10, CXCL11, IL-1a, IL-1β, and IL-1 receptor agonists (IL-1ra), GM-CSF, osteopontin, and VEGF. The graphs are presented as mean±s.d. for each individual values. Student's t-test was used and indicates $p<0.05$ and **indicates $p<0.01$.
Figure 16B:
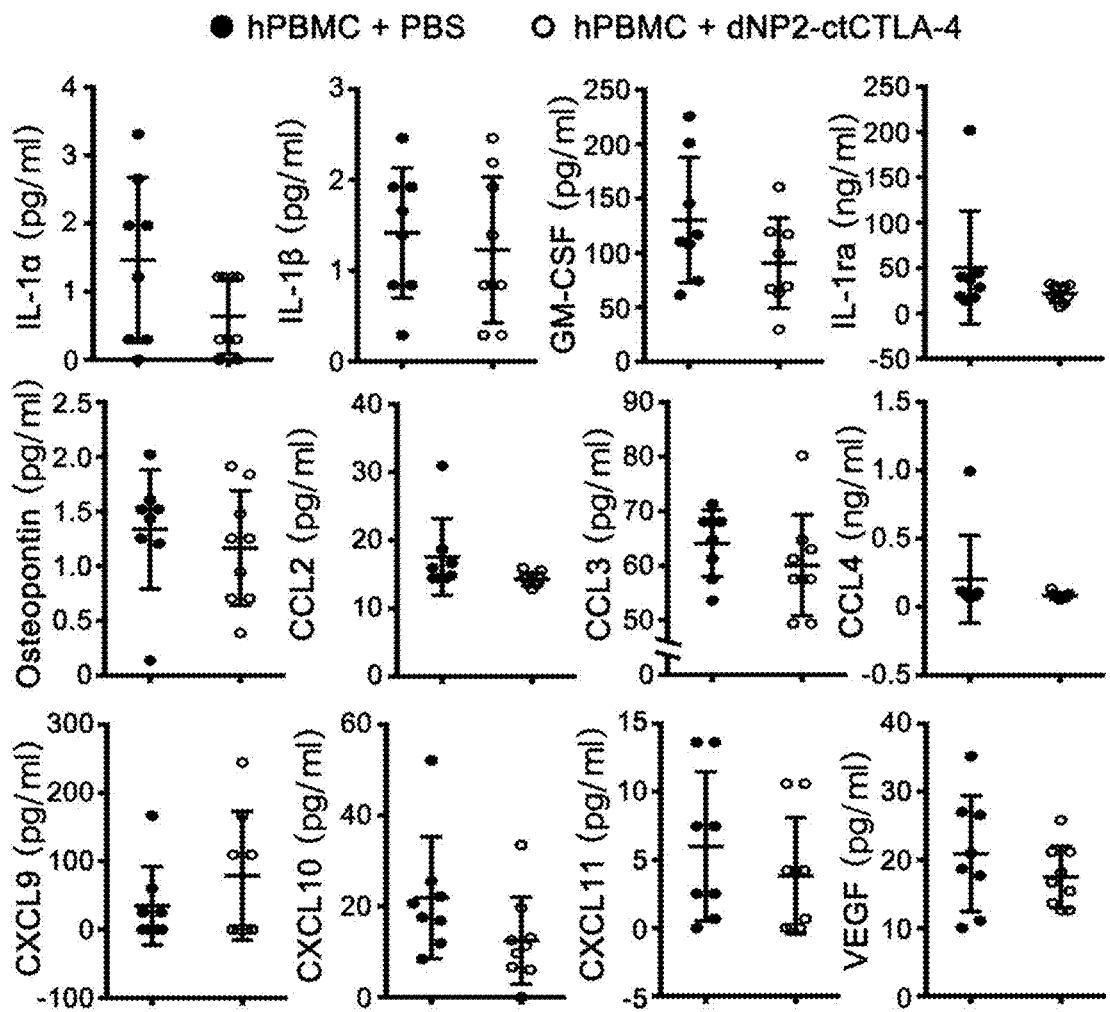

Inhibitory Activity Against T Cells-Associated Blood Circulation Cytokine in Mice Referring to FIGS. 16A and 16B, serum from HUVEC-collagen tissue allografted mice was analyzed in a multiplex Luminex assay to analyze serum concentrations of IFN-γ, IL-17A, TNFa, CCL2, CCL3, CCL4, CXCL9, CXCL10, CXCL11, IL-1a, IL-1β, and IL-1 receptor agonists (IL-1ra), GM-CSF, osteopontin, and VEGF. The graphs are presented as mean±s.d. for each individual values. Student's t-test was used and * indicates $p<0.05$ and ** indicates $p<0.01$.

To further evaluate the in vivo mechanism of dNP2-ctCTLA-4 action to prevent graft rejection, we analyzed the serum of mice to investigate inflammatory cytokine and chemokine levels. dNP2-ctCTLA-4-treated mice showed significantly reduced levels of IFN-γ, IL-17A, and TNF-a, which are known to be secreted mainly by activated T cells in this model (FIG. 16a). Other cytokines and chemokines mainly produced by endothelial cells or APCs were not affected by dNP2-ctCTLA-4 treatment, such as IL-1a, IL-1β, GM-CSF, IL-1ra, osteopontin, CCL-2, -3, -4, CXCL-9, CXCL-10, CXCL-11, and VEGF (FIG. 16b). To further confirm the possibility of dNP2-ctCTLA-4 function in other cells, we examined major histocompatibility complex (MHC) molecule expression on HUVEC cell surfaces, which is induced by in vitro cytokine stimulation, and found that there was no significant change. In addition, in vitro treatment of dNP2-ctCTLA-4 to FACS-sorted CD14 positive human primary monocytes and CD19 positive B cells did not alter mRNA expression of IL-6, IL-8, and IL-1β upon LPS stimulation. Taken together, these results suggest that prevention of human skin or HUVEC graft rejection by treatment with dNP2-ctCTLA-4 is mainly be due to successful modulation of allogeneic T cell activation.

Conclusion

The cytoplasmic domain of dNP2-conjugated recombinant CTLA-4 having the function of significantly controlling T cells even without ligand interactions was identified by the present invention. This demonstrated that dNP2-ctCLTA-4 is capable of controlling human T cell activation and effector functions in human skin or HUVEC graft model. Unlike conventionally known CTLA-4-Ig, it can be seen that the composition of the present invention can effectively control memory T cells, although it receives costimulation through other ligands.

In addition, fusion products (conjugates), in which ctCTLA-4 proteins are combined with cell-penetrating peptides according to the present invention, were identified, which inhibit activation of T cells and exhibit effective therapeutic effects in skin allograft models, which means that the conjugates are more significantly delivered to memory or activated CD4 and CD8 T cells than naive cells.

Then, dNP2-ctCTLA-4 fusion products (conjugates) were analyzed in FACS-sorted CD45RA⁺CD45RO human naive T cells and CD45RA CD45RO⁺ memory T cells. Results showed that dNP2-ctCTLA-4 fusion products have an effect of significantly inhibiting IFN-γ expression by memory T cells and naive T cells upon TcR stimulation.

This suggested that the dNP2-ctCLTA-4 fusion products according to the present invention inhibit secretion of IFN-γ and IL-17 upon infiltration of blood of graft tissues and T cells, thereby controlling functions of effector T cells.

Although various graft rejection suppressors were conventionally developed, mTOR inhibitors, corticosteroid and the like cause toxicity-associated problems and undesired problems affecting cells occurred. Although anti-CD3 monoclonal antibody (mAb) Muronomab-CD3, anti-CD25 mAb Daclizumab, anti-CD52 mAb Alemtuzumab, and B-lymphocyte stimulator (BLyS)-inhibiting mAb Belimumab have effective therapeutic effects, they have very serious side-effects of the increased risk of infection by lymphocyte deficiency mechanism. Belatacept was effective in reducing graft rejection, but blocked interactions between APC and T cells, thus causing side effects of urinary tract infection.

In contrast, the ctCTLA-4 and dNP2-ctCLTA-4 fusion products of the present invention directly inhibit T cell responses without altering APC or endothelial cells, and thus have advantages of having fewer side effects, being more stable and having a frequency of circulating CD4$^+$ Foxp3$^+$ regulatory T cells. In conclusion, the dNP2-ctCTLA-4 fusion products of the present invention are significantly advantageous over conventional immunomodulators in terms of mechanism and effects.

The dNP2-ctCTLA-4 fusion products strongly inhibit the production and proliferation of cytokines of both naive and memory human CD4 and CD8 T cells, which means that they can regulate the progression of graft rejection symptoms or promote recovery thereof without in vivo toxicity.

In summary, in the present invention, novel and efficacious fusion products (conjugates) in which ctCTLA-4 peptides and ctCTLA-4 peptides are linked to cell-penetrating peptides have been developed. It was clearly found that these peptides, fragments thereof or fusions (conjugates) thereof have a remarkably high delivery efficiency to human T cells, and significantly inhibit activation, proliferation and reaction of homologous human T cells such as production of inflammatory cytokines.

In addition, it was found that the fusion products (conjugates) are effective in reducing skin graft damage in vivo and increasing graft success rates, in particular, dNP2-ctCTLA-4 fusion products (conjugates) have the most optimal efficiencies and stability.

The invention claimed is:

1. A method for inhibiting transplant rejection in a subject in need thereof, comprising administering a composition to the subject, (a) before transplant or (b) after transplant, wherein the composition comprises a fusion product, as an effective ingredient, said fusion product comprising a peptide comprising the amino acid sequence of SEQ ID NO: 4 and a cell-penetrating peptide.

2. The method according to claim 1, wherein the cell-penetrating peptide comprises any one selected from the group consisting of HIV-1 tat (47-57), D-amino acid-substituted HIV-1 tat (47-57), arginine-substituted HIV-1 tat (47-57), *Drosophila* Antennapaedia (43-58), a virus RNA-bound peptide including 7 or more amino acids, a DNA-bound peptide including 7 or more arginines, a polyarginine polypeptide including 6 to 8 arginines, and a peptide comprising any one sequence of SEQ ID NOs: 8-20.

3. The method according to claim 1, wherein the transplant rejection is a transplant rejection of skin, blood, cornea, liver, lung, intestines, pancreas, heart, kidney, bone marrow, stem cells, or progenitor cells.

4. The method according to claim 1, wherein the transplant rejection is graft-versus-host rejection.

5. The method according to claim 1, wherein the cell-penetrating peptide comprises the amino acid sequence of SEQ ID NO: 8, 9, or 10.

* * * * *